(12) United States Patent
Fisher

(10) Patent No.: US 7,338,767 B1
(45) Date of Patent: Mar. 4, 2008

(54) USE OF MICROPHTHALMIA FOR DIAGNOSIS, PROGNOSIS AND/OR TREATMENT OF MELANOMA

(75) Inventor: David E. Fisher, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/229,283

(22) Filed: Jan. 13, 1999

Related U.S. Application Data

(60) Provisional application No. 60/071,420, filed on Jan. 14, 1998.

(51) Int. Cl.
*G01N 33/53* (2006.01)
*G01N 33/567* (2006.01)
*G01N 33/574* (2006.01)

(52) U.S. Cl. ............... 435/7.1; 435/7.21; 435/7.23
(58) Field of Classification Search ............... 536/23.1; 435/4, 6, 7.1
See application file for complete search history.

(56) References Cited

U.S. PATENT DOCUMENTS

| 5,009,995 A | 4/1991 | Albino et al. | 435/7.23 |
|---|---|---|---|
| 5,605,831 A | 2/1997 | Vielkind | 435/344 |
| 5,674,492 A | 10/1997 | Armitage et al. | 424/144.1 |

FOREIGN PATENT DOCUMENTS

WO   WO 97/39774   10/1997

OTHER PUBLICATIONS

Yasumoto et al (Pigment Cell Research, 1998, 11(6):329-336).*
Shibahara et al (J. Invest. Derm. Symp. Proc., 1999, 4(2):202-204).*
Zimmer (Cell Motility and the Cytoskeleton, 1991, 20:325-337).*
Eriksson et al (Diabetologia, 1992, 35:143-147).*
Powell et al (Pharmacogenesis, 1998, 8:411-421).*
Carrere et al (Gut, 1999, 44:550-551).*
Vallejo et al (Biochimie, 2000, 82:1129-1133).*
Guo et al 9J. Pharm. Exp. Ther., 2002, 300:206-212).*
Jang et al (Clin. Exp. Metastasis, 1997, 15:469-483).*
Weilbaecher et al (J. Exp. Med., 1998, 187:755-785) (Electronic 1-22).*
Hemesath et al (Nature, 1998, 391:298-301) (Electronic 1-7).*
Oda et al (Histopathology, 2001, 39:629-637).*
He et al (Zhongguo Gonggong Weisheng, 2001, 17:675-677, abstract).*
Su et al (Zhounghua yi xue za zhi, 1995, 75:144-146, abstract).*
Ladanyi et al, CRISP 5R01CA095785-03.*
S. Sato et al., *Oncogene*, 14:3083-3092 (1997).
H. Kahn et ak., *A.J.C.P.*, 79(3):341-347 (1983).

* cited by examiner

*Primary Examiner*—Susan Ungar
(74) *Attorney, Agent, or Firm*—Nixon Peabody LLP

(57) ABSTRACT

Microphthalmia (Mi) while present in melanocytes, a cells and osteoclast, is not normally present in other cells. We have found that Mi is present in the nucleus of melanoma cells. Melanoma can be diagnosed by contacting a malignant cell with a probe for Mi. If the probe identifies Mi in the nucleus of the cell, the cell is a melanoma.

5 Claims, 10 Drawing Sheets

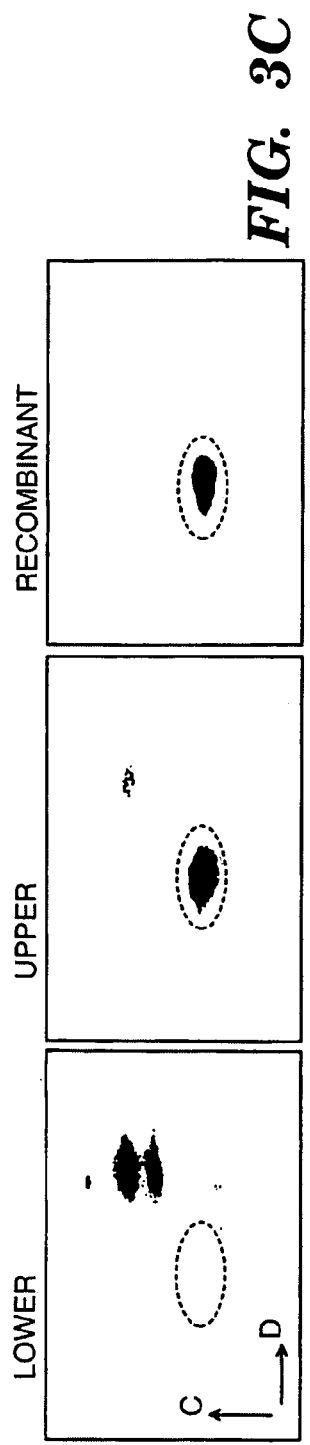
FIG. 3C
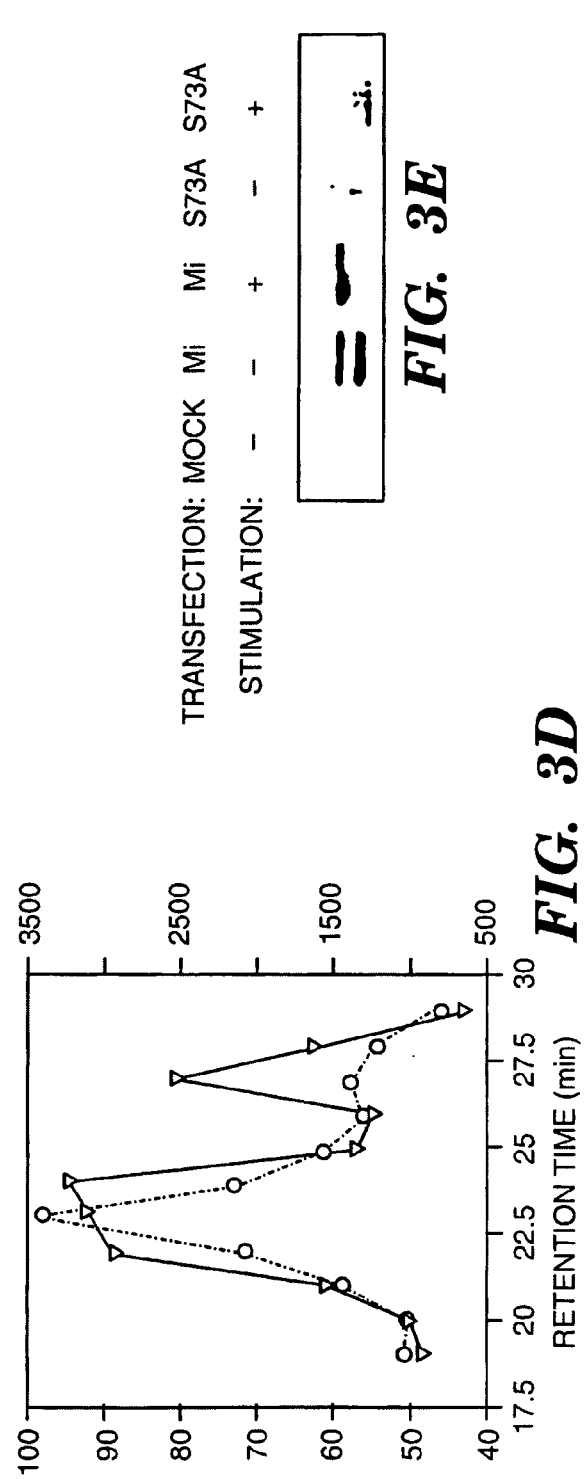
FIG. 3E
FIG. 3D

USE OF MICROPHTHALMIA FOR DIAGNOSIS, PROGNOSIS AND/OR TREATMENT OF MELANOMA

CROSS-REFERENCE TO RELATED APPLICATIONS

This application claims benefit of provisional application 60/071,420, filed Jan. 14, 1998, now abandoned.

The present invention involved government funding under NIH grant AR43369 and the U.S. government has certain rights therein.

FIELD OF THE INVENTION

The present invention is directed to methods for diagnosis and/or prognosis of melanoma in individuals using microphthalmia as a marker.

BACKGROUND OF THE INVENTION

Melanoma has been on the rise for decades. It is presently the seventh most common cancer in the United States. It is currently estimated that by the year 2000 the lifetime risk of developing skin melanoma in Americans will be 1 in 75. The annual incidence of human melanoma worldwide is increasing at the rate of approximately 5% per year (16,17). Due to its propensity to metastasize early, coupled to the common feature of late recurrence, relapses from melanoma represent an important and often life threatening clinical condition. The cancer starts in the skin, but frequently spreads. It can spread locally or throughout the body. Tissues with melanomas can include lymph glands, liver, bones, brain, lung, adrenal glands, the spinal cord, and vertebrae. Although, once melanoma has spread beyond the original skin site it is currently considered incurable, there are treatment modalities that can prolong an individual's survival.

Metastatic diseases of unknown origin are fairly common. Melanoma resides among the tumor types more commonly associated with metastases lacking an obvious primary tumor site (18-22). It has proven difficult to determine if such metastatic tissue is melanoma. One of the problems is that when a melanoma is not found on the skin, its diagnosis is problematic. Currently, there are two markers typically used to diagnose melanoma. These markers have problems because the first marker, S100, while sensitive and present in about 80% of melanoma, is also widely present in non-melanoma tumors [Kahn, H. J., et al., *American J. of Clin. Pathol.* 79:341-471 (1983). Thus, it also stains a significant number of nonmelanoma malignancies. The second marker, HMB-45, while very specific for melanoma, only detects about 50% of melanomas [*Applied Immunolohistochemistry* 4:73-95 (1996)]. Other estimate for HMB-45 have ranged as low as 5% and it has been suggested that it stains variably in a technique-dependent fashion (23, 27, 29, 30, 32-35). Thus, there is a need for other markers that will specifically detect melanoma.

Determining the origin of a metastatic tissue arising from a melanoma is extremely difficult. For example, a skin melanoma can be removed, yet come back years later at a different site. Conversely, the fact that someone had a melanoma removed 20 years ago, does not mean that a metastatic disease of unknown origin would necessarily be a melanoma because that individual could have developed a different cancer. Thus, the ability to determine the origin of a metastatic disease is very important because it can affect the diagnosis and/or the type of treatment regime prescribed.

It would be extremely important if a better and more accurate means for diagnosing melanoma was available. It would also be important having a better means to determine prognosis.

Another problem with melanomas involves the treatment thereof. It is important to be able to selectively treat the malignant tissue and not the surrounding normal tissues. Side effects are frequently experienced from current treatments because some normal tissue is also harmed. Means for improving the selectivity are desired.

SUMMARY OF THE INVENTION

We have now discovered an improved method that can be used for diagnosis of melanoma. We have discovered that the transcription factor microphthalmia (Mi) is an excellent marker that when present in a malignant tissue is diagnostic of melanoma. Mi is normally present in melanocytes, mast cells, and osteoclasts. However, it is typically not present in other cells. Thus, by obtaining a biological specimen, wherein the specimen is preferably a malignant tissue and measuring for the presence of Mi, by looking at the protein or transcript for Mi, one has a simple method for the diagnosis of melanoma, wherein the presence of Mi is indicative of melanoma.

Additionally, by looking at the quantity of Mi, present in the cell and/or its state, i.e., activated vs. non-activated, one can use Mi prognostically.

Finally, one can take advantage of Mi's correlation with melanoma for a method of treatment. For example, by selectively targeting Mi one is in effect selectively targeting melanoma.

BRIEF DESCRIPTION OF THE FIGURES

In FIG. 1A, 501mel cells were exposed to SI (20 ng/ml) or TPA (10 ng/ml) for the indicated times and total protein blots were probed for Mi (top), phosphotyrosine (center), and ERK-1/ERK-2 (anti-MAPK, bottom). Bands that reacted with anti-Kit and anti-ERK antibodies are indicated. MAPK activation correlates with the Mi mobility shift. FIG. 1B shows reversal of the Mi mobility shift with phosphatase. Mi immunoprecipitates from SI-stimulated cells were treated with increasing amounts of phosphatase followed by Western blotting. Phosphatase inhibitors (final lane) prevent the reversal of the mobility shift.

FIG. 2A shows that phosphoamino acid analysis of Mi upper band reveals only phosphoserine residues. Mi from $^{32}$P-labeled cells was immunoprecipated and the upper band was subjected to acid hydrolysis followed by phosphoamino acid analysis by thin layer chromatography. Migration of phosphoamino acid standards are shown at the right. FIG. 2B shows the effect of MEK inhibition on the Kit- and TPA-stimulated Mi phosphorylation. 501mel cells were stimulated by SI or TPA in the presence of the indicated amounts of the MEK inhibitor, followed by detection with antibodies against Mi (top) or phospho-MAPK (bottom).

FIGS. 3A-3E show Mi phosphorylation at S73 by MAPK. FIG. 3A, Lysates from +/−SI stimulated melanoma cells were immunoprecipitated (anti-ERK-2 or control) and tested in IVK using N-terminal (N) or C-terminal (C) recombinant Mi substrates or MBP. FIG. 3B, Mutations in Mi were tested as IVK substrates from +/−SI cell extracts immunoprecipitated with anti-ERK and identified Ser73 as phosphoacceptor. FIG. 3C, 2D tryptic maps from $^{32}$p labeled endogenous cellular Mi lower and upper bands revealed a distinct Kit-dependent spot (hatched circle) which comigrates with ERK/IVK phosphorylated Mi. "c" and "e" refer to chromatographic and electrophoretic migration. FIG. 3D, HPLC fractionation of in vivo $^{32}$P-labeled Mi tryptic digests from upper band (open diamonds) shows coelution with ERK/IVK recombinant Mi (filled triangles). Y axes indicate beta counts. The secondary peak likely results from oxidative peptide bond cleavage from performic acid (N. Ahn et al., Curr. Opin. Cell Biol. 4, 992-999 (1992)). FIG. 3E shows wild type or S73A mutant Mi were transfected into COS-7 cells followed by TPA stimulation as indicated. S73A fails to undergo mobility shift.

FIG. 4A, wild type or S73A mutant Mi were co-transfected with minimal or tyrosinase promoter-driven luciferase reporters into BHK cells. Constitutively active Raf and wild type MEK were included as indicated to activate the MAP kinase pathway. Mean fold activation (normalized to 100% for activity of wild type Mi in the absence of Raf/MEK, column 8) from three independent experiments is shown with standard error bars. Raf/MEK potentiates transactivation by wild type but not S73A Mi. FIG. 4B, Model for signal transduction from Kit to Mi. Tissue-specific factors are shown in grey boxes.

FIG. 5A shows RT-PCR of Mi in neuroblastoma and melanoma cell lines. Mi product migrates as a doublet at 432 bp and 448 bp (18-bp alternative splice (11)). Neuroblastomas were PCR negative while melanomas were positive. FIG. 5B shows Western blot showing 52 and 56 Kd isoforms of Mi protein (12) (absent in NIH3T3). Steel factor (c-Kit ligand) stimulation of the cell line 501-mel causes phosphorylation of the 52 Kd species as described (12). FIG. 5C is nuclear immunostaining of 501-mel cells with D5 Mi antibody. Control lacked primary antibody. 10× and 60×refer to magnification.

DETAILED DESCRIPTION OF THE INVENTION

Figure 1A:
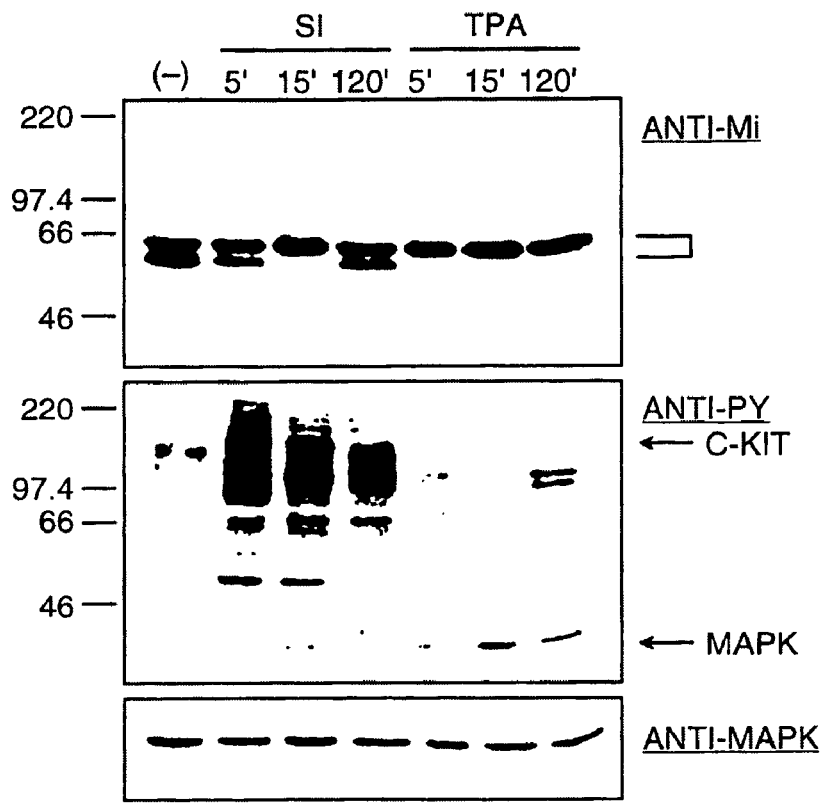
FIGS. 1A and 1B show Kit-induced Mi phosphorylation.

Mi is a basic/helix-loop-helix/leucine zipper (b-HLH-ZIP) transcription factor implicated in pigmentation, mast cells and bone development. Mi is essential to the development and survival of melanocytes.

The gene encoding mouse Mi was cloned in 1993 and found to encode a Myc-related b-HLH-ZIP protein. [Hughes, J. J. et al., J. Biol. Chem. 268:20687-20690 (1993); Hodgkinson, C. A. et al., Cell 74: 395-404 (1993)] Biochemical studies demonstrated a DNA binding specificity for consensus sequence CA(C/T)(G/A)TG and its capacity to heterodimerize in vitro with three structurally related b-HLH-ZIP factors, TFEB, TFE3, and TFEC, but not Myc/Max, USF or other b-HLH-ZIP proteins. [Hemesath, T. J., Genes & Dev. 8: 2770-2780 (1984); Carr, C. S., et al., Mol. Cell Biol., 10: 4384-4388 (1990); Beckman, H., Genes & Dev., 4: 167-179 (1990); Roman, C. A., Mol. Cell Biol. 12(2): 817-827 (1992); Zhao, G. Z., et al., Mol. Cell. Biol., 13: 4505-4512 (1993); Yasumoto, K., et al., Biochimica et. Biophysica Acta, 1353: 23-31 (1997); Blackwood, E. M., Science, 251: 1211-1217 (1991)] Mi/Mi mutant mice display defective eye development (related to pigment cell abnormalities), complete lack of skin melanocytes, deafness related to absent of pigment cells in the inner ear (stria vascularis)), severe defects in mast cells, and osteoporosis. Mutations in human Mi have been detected in the autosomal dominant hereditary deafness and pigmentation condition, Waardenburg syndrome, type 2A [Tassabehji, et al., Nature Genet., 8:251-255 (1994); Hughes, A. E. et al., Nature Genet., 7:509-512 (1994)] (a condition characterized by a white forelock and deafness). The Mi gene (4) encodes a transcription factor (5) which regulates expression of the pigmentation enzymes tyrosinase, TRP1, and TRP2 (5-7). Recent studies have demonstrated that Melanocyte Stimulating Hormone (α-MSH) upregulates pigmentation through stimulation of Mi expression (8, 9).

While Mi may regulate pigmentation, the complete absence of melanocytes in Mi-deficient mice suggests that Mi is essential for melanocyte development or postnatal survival, or both. One instructive mouse mutant, mi$^{vit}$ displays nearly normal melanocyte development, but accelerated age-dependent melanocyte death over the first months of life (10). This death is attributable to a mutation within the helix-loop-helix motif of mi (5, 11) and suggests a vital role for Mi in post-natal survival of melanocytes. One potential clue to Mi's survival role comes from evidence that the Steel/Kit cytokine pathway (whose deficiency produces identical absence of melanocytes) regulates MAP kinase-mediated phosphorylation of Mi (12). This produces transcriptional super-activation by Mi protein through selective recruitment of CBP/p300 (13), a family of transcriptional coactivators for Mi (14, 15).

Various abnormalities in Mi have been connected to pigmentation deafness and osteoporosis as stated above. However, its correlation with melanoma cells has heretofore been unknown. For example, Mi is involved in a signaling pathway linked to Kit signaling. However, the presence of Kit does not correlate with melanoma, despite the fact that Kit is an oncogene. We have now discovered that there is a high correlation between the presence of Mi in a malignant cell and that cell being a melanoma. We have been able to determine that Mi is specific for melanoma. For example, we have looked at numerous malignant tissues including many brain tissues and found that Mi was not present. The negative Mi staining tumors include basal cell carcinoma, squamous cell carcinoma, atypical fibroxanthoma, granular cell tumor, Schwannoma and neurofibroma. Thus, by looking for the presence of Mi one is able to determine the origin of the cell and use such information to determine the course of treatment.

Mi staining in melanomas produces a nuclear pattern which has some theoretical advantages over cytoplasmic immunostains. It may be difficult to distinguish background staining from positivity for cytoplasmic antibodies, especially with weak signal. Furthermore, cellular architecture is not obscured with nuclear staining which aids in the preservation of the tissue structure being examined. For pigmented lesions it may be difficult to distinguish cytoplasmic stains from pigmentation, although such lesions are less likely to require special stains.

In one series of experiments, Mi was expressed in 8/8 histologic amelanotic melanomas. Based on its recognition of the M box promoter element (5), Mi is thought to regulate transcription of the pigmentation enzymes tyrosinase, TRP1 and TRP2 (5-7). Its persistent expression in the amelanotic melanomas examined here suggests that factors downstream of Mi may downregulate pigmentation. One such mechanism is the proteolytic degradation of tyrosinase, recently described for human melanoma cells (25). These findings suggest that downregulation of pigmentation is beneficial to melanoma cells and that rather than loss of Mi itself, mechanisms downstream of Mi may more commonly occur. Of note, nondetection of Mi expression at the RNA level has been observed in a murine amelanotic melanoma cell line (15).

Mi is a sensitive marker for this clinical entity, which can represent a diagnostic challenge. Due to its propensity for vertical growth, malignant melanoma may metastasize at an early stage, even before a primary cutaneous lesion is identified (as occurs in 5-14% of cases(18-22)). Moreover since a significant fraction of metastatic melanomas are amelanotic, such lesions may be difficult to classify on simple morphologic grounds, certainly to the non-specialist, and could represent a variety of undifferentiated or poorly differentiated tumors such as epithelial tumors, sarcomas, lymphoid neoplasms or germ cell tumors (38). Combined detection of S-100 and Keratin may help rule in or out the possibility a melanoma. S-100 is sensitive for melanoma, but commonly stains other tumors in this differential including breast adenocarcinomas, lung carcinomas, teratomas, neurogenic tumors, and others (23, 29) (39-42), whereas Keratin expression is atypical in melanomas (43).

2 of the breast cancer specimens produced cytoplasmic Mi staining. Mi is expressed in osteoclasts (37), and many breast cancers express genes involved in bone resorption such as PTH-rp, cathepsin K, IL-6, IL-1, TGF, and collagenases (44, 45). Mi may upregulate osteoclast-like genes such as cathepsin K, a resorption factor recently detected in breast tumor lines (46). As such, Mi expression may play a role in bone metastasis of breast cancer, perhaps even predicting osteotrophism. Accordingly, targeting Mi expression may also be useful in treating and/or diagnosing breast cancer.

Mi was not detected in 9 desmoplastic/neurotropic melanomas. Desmoplastic melanomas account for less than 1% of melanomas and often arise in association with lentigo maligna (47). About 20-30% of these tumors lack an in situ component. Desmoplastic tumors tend to grow as a fibrous nodule, frequently track along nerves, and have a distinct clinical behavior compared with other melanomas. HMB-45 is often negative in desmoplastic melanomas, but S-100 is usually positive. While this tumor is classified as a melanoma, there is some debate as to the origin and true biology of the spindle cells (48-50), and lack of Mi is believed to be notable.

Metastatic melanoma tissue can be present throughout the body and such locations typically include lymph glands, liver, bones, brain, lung, adrenal glands, spinal cord and vertebrae. However, malignant tissues present in such sites can be from numerous types of cancers. Thus, obtaining a biological sample and looking for the presence of Mi is important in being able to diagnose the tissue as a melanoma. Since Mi is normally present in melanocytes, mast cells and osteoclasts, the biological specimen preferably does not include those cells.

Standard detection techniques well known in the art for detecting proteins, RNA, DNA, and peptides can readily be applied to detect Mi or its transcript.

Such techniques may include detection with nucleotide probes or may comprise detection of the protein by, for example, antibodies or their equivalent. Preferably, the nucleotide probes may be any that will selectively hybridize to Mi. For example, it will hybridize to Mi transcript more strongly than to other naturally occurring transcription factor sequences. Types of probes include cDNA, riboprobes, synthetic oligonucleotides and genomic probe. The type of probe used will generally be dictated by the particular situation, such as riboprobes for in situ hybridization, and cDNA for Northern blotting, for example. Detection of the Mi encoding gene, per se, will be useful in screening for conditions associated with enhanced expression. Other forms of assays to detect targets more readily associated with levels of expression—transcripts and other expression products will generally be useful as well. The probes may be as short as is required to differentially recognize Mi mRNA transcripts, and may be as short as, for example, 15 bases, more preferably it is at least 17 bases. Still more preferably the Mi probe is at least 20 bases.

A probe may also be reverse-engineered by one skilled in the art from the amino acid sequence of Mi. However use of such probes may be limited, as it will be appreciated that any one given reverse-engineered sequence will not necessarily hybridize well, or at all with any given complementary sequence reverse-engineered from the same peptide, owing to the degeneracy of the genetic code. This is a factor common in the calculations. of those skilled in the art, and the degeneracy of any given sequence is frequently so broad as to yield a large number of probes for any one sequence.

The form of labeling of the probes may be any that is appropriate, such as the use of radioisotopes, for example, $^{32}$p and $^{35}$S. Labeling with radioisotopes may be achieved, whether the probe is synthesized chemically or biologically, by the use of suitably labeled bases. Other forms of labeling may include enzyme or antibody labeling such as is characteristic of ELISA.

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabelled cDNA or RNA is then hybridized to the preparation, washed and analyzed by autoradiography.

In situ hybridization visualization may also be employed, wherein a radioactively labeled antisense cRNA probe is hybridized with a thin section of a biopsy sample, washed, cleaved with RNase and exposed to a sensitive emulsion for autoradiography. The samples may be stained with haematoxylon to demonstrate the histological composition of the sample, and dark field imaging with a suitable light filter shows up the developed emulsion. Non-radioactive labels such as digoxigenin may also be used.

Immunohistochemistry is preferably used to detect expression of human Mi in a biopsy sample. A suitable antibody is brought into contact with, for example, a thin layer of cells, washed, and then contacted with a second, labeled antibody. Labeling may be by enzyme, such as peroxidase, avidin or by radiolabelling. Chromogenic labels are generally preferable, as they can be detected under a microscope. Mi is a nuclear protein and provides a good staining pattern.

More generally preferred is to detect the protein by immunoassay, for example by ELISA or RIA, which can be extremely rapid. Thus, it is generally preferred to use antibodies, or antibody equivalents, to detect Mi.

It may not be necessary to label the substrate, provided that the product of the enzymatic process is detectable and characteristic in its own right (such as hydrogen peroxide for example). However, if it is necessary to label the substrate, then this may also comprise enzyme labeling, labeling with radioisotopes, antibody labeling, fluorescent marker labeling or any other suitable form which will be readily apparent to those skilled in the art.

Antibodies may be prepared as described below, and used in any suitable manner to detect expression of Mi. Antibody-based techniques include ELISA (enzyme linked immunosorbent assay) and RIA (radioimmunoassay). Any conventional procedures may be employed for such immunoassays. The procedures may suitably be conducted such that: a Mi standard is labeled with a radioisotope such as $^{125}$I or $^{35}$S, or an assayable enzyme, such as horseradish peroxidase or alkaline phosphatase and, together with the unlabelled sample, is brought into contact with the corresponding antibody, whereon a second antibody is used to bind the first and radioactivity or the immobilized enzyme assayed (competitive assay); alternatively, Mi in the sample is allowed to react with the corresponding immobilized antibody, radioisotope- or enzyme-labeled anti-Mi antibody is allowed to react with the system and radioactivity or the enzyme assayed (ELISA-sandwich assay). Other conventional methods may also be employed as suitable.

For example using a monoclonal antibody to Mi resulted in strong nuclear staining within melanocytes, nevi, dysplastic nevi, melanoma in situ, and 100% of 76 consecutively acquisitioned melanomas, including amelanotic and metastatic tumors. In side by side comparisons Mi stained tumors which were negative for HMB-45 or S100. Among nonmelanoma tumors, Mi stained cytoplasms in two of 81 cases, and no cases exhibited nuclear staining. Thus, Mi is a sensitive and specific marker for melanoma.

The above techniques may be conducted essentially as a "one-step" or "two-step" assay. The "one-step" assay involves contacting antigen with immobilized antibody and, without washing, contacting the mixture with labeled antibody. The "two-step" assay involves washing before contacting the mixture with labeled antibody. Other conventional methods may also be employed as suitable.

Enzymatic and radio-labeling of Mi and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect Mi according to preference. One such technique is Western blotting (Towbin et at., *Proc. Nat Acad. Sci* 76:4350 (1979)), wherein a suitably treated sample is run on an SDS-PAGE gel before being transferred to a solid support, such as a nitrocellulose filter. Anti-Mi antibodies (unlabelled) are then brought into contact with the support and assayed by a secondary immunological reagent, such as labeled protein A or anti-immunoglobulin (suitable labels including $^{125}$I, horseradish peroxidase and alkaline phosphatase).

Samples for diagnostic purposes may be obtained from any number of sources. A sample obtained directly from the tumor, such as the stroma or cytosol, may be used to determine the origin of the tumor. It may also be appropriate to obtain a sample from other biological specimens, where Mi is present. Such diagnosis may be of particular importance in monitoring progress of a patient, such as after surgery to remove a tumor. If a reference reading is taken after the operation, then another taken at regular intervals, any rise could be indicative of a relapse, or possibly a more severe metastasis. Preferably, the sample is from the tumor itself.

Mi binds E box-type enhancer elements and may heterodimerize with the related family members TFEB, TFEC and TFE3 (Hemesath, T. J., et al., *Genes Dev.* 8, 2770-80 (1994)). Mutations in c-Kit or its ligand Sl (stem cell factor, mast cell growth factor) similarly result in animals lacking melanocytes and functional mast cells, along with defects in hematopoiesis and germ cell development (Russell, E., *Adv. Genet.* 20, 357-459 (1979). 3. Witte, O. Steel, Cell 63, 5 (1990)). This striking phenotypic overlap has led to suggestions that Sl, c-Kit, and Mi function in a common growth/differentiation pathway (Steingrimsson, E., et al., *Nature Genet.* 8, 256-63 (1994); Dubreuil, P., et al., *Proc. Natn. Acad. Sci. U.S.A.* 88, 2341-2345 (1991)). Germline mutations at loci encoding the transcription factor Mi, the cytokine receptor c-Kit, and its ligand Steel factor (Sl) result in strikingly similar defects in mast cell and melanocyte development (Moore, K. J., *Trends Genet.* 11, 442-8 (1995); Russell, E., *Adv. Genet.* 20, 357-459 (1979); Witte, O. Steel, Cell 63, 5 (1990).

We found a biochemical Link between Kit signaling and the activity of Mi. Stimulation of melanoma cells with SI results in activation of MAP kinase, which in turn phosphorylates Mi at a consensus target serine. This phosphorylation upregulates Mi transactivation of the tyrosinase pigmentation gene promoter. In addition to modulating pigment production, such signaling may regulate the expression of genes essential for melanocyte survival and development. The pathway represents a novel use of the general MAP kinase machinery to transduce a signal between a tissue-specific receptor at the cell surface and a tissue-specific transcription factor in the nucleus.

The antibodies may be raised against either a peptide of Mi or the whole molecule. Such a peptide may be presented together with a carrier protein, such as an KLH, to an animal system or, if it is long enough, say 25 amino acid residues, without a carrier. Preferred peptides include regions unique to Mi.

Polyclonal antibodies generated by the above technique may be used direct, or suitable antibody producing cells may be isolated from the animal and used to form a hybridoma by known means (Kohler and Milstein, *Nature* 256:795. (1975)). Selection of an appropriate hybridoma will also be apparent to those skilled in the art, and the resulting antibody may be used in a suitable assay to identify Mi.

This invention also provides a convenient kit for detecting human Mi levels. This kit includes a probe for Mi such as antibodies or antibody fragments which selectively bind human Mi or a set of DNA oligonucleotide primers that allow synthesis of cDNA encoding human Mi. Preferably, the primers comprise at least 10 nucleotides, more preferably at least about 20 nucleotides, and hybridizes under stringent conditions to a DNA fragment having the human Mi sequence nucleotide. The kit will contain instructions indicating how the probe can be used diagnostically or prognostically. As herein used, the term "stringent conditions" means hybridization will occur only if there is at least 95% and preferably at least 97% homology between the sequences.

Homology is measured by means well known in the art. For example % homology can be determined by any standard algorithm used to compare homologies. These include, but are not limited to BLAST 2.0 such as BLAST 2.0.4 and i. 2.0.5 available from the NIH (Altschul, S. F., et al. Nucleic Acids Res. 25: 3389-3402 (1997)) and DNASIS (Hitachi Software Engineering America, Ltd.). These programs should preferably be set to an automatic setting such as the standard default setting for homology comparisons. As explained by the NIH, the scoring of gapped results tends to be more biologically meaningful than ungapped results.

One can also take advantage of Mi's correlation with melanoma to treat melanoma. Thus, one can screen for and select compounds, preferably small molecules that selectively react with Mi. These compounds can then be used to provide selective targeting of the melanoma. For example, the small molecule could be cytotoxic. In another embodiment, the compound, e.g. a cytotoxic compound such as ricin could bind to Mi and be activated so that the molecule serves as a target or catalyst for a second compound that it used to treat a melanoma.

All references cited above or below are herein incorporated by reference.

The following Examples serve to illustrate the present invention, and are not intended to limit the invention in any manner.

EXAMPLES

Immunoprecipitation (IP) and Western Blot Analysis.

The monoclonal antibody D5 was raised against a histidine fusion protein expressed from the amino terminal Taq-Sac fragment of human MITF cDNA (Tachibana, M., et al., Hu. *Mol. Genet.* 3, 553-7 (1994)) and produces a specific gel mobility supershif with Mi, but not with the related proteins TFEB, TFEC, and TFE3 (not shown). 501mel cells (gift of Dr. Ruth Halaban, Yale University) were maintained in F10 medium plus 10% fetal calf serum (FCS). Cells were stimulated with 20 ng/ml recombinant human SI (R&D Systems) or 10 ng/ml TPA for eight minutes at 37° C. unless otherwise indicated. Cells were lysed in 50 mM Tris pH 7.6, 150 mM NaCl, 10% Triton-X 100 plus protease and phosphatase inhibitors. Samples were solubilized in SDS sample buffer plus 0.5% 2-mercaptoethanol and boiled for 5 minutes. Following SDS/PAGE and transfer to nitrocellulose, blots were blocked in 5% milk/0.05% Tween-20 in Tris-buffered saline prior to antibody incubation. Proteins were detected with peroxidase-conjugated second-step antibody (Cappel) and chemiluminescence reagents (Amersham).

Phosphatase Treatment.

Immunoprecipitated Mi washed three times with lysis buffer, twice with Buffer A (100 mM KCl, 20 mM Hepes pH 7.4, 0.2 mM EDTA, 2 mM DTT, plus protease inhibitors), and resuspended in 40 µl Buffer A. Control digests contained phosphatase inhibitors sodium vanadate (1 mM), sodium pyrophosphate (20 mM), and sodium fluoride (10 mM). Potato acid phosphatase (Boehringer Mannheim) was added to IPs for 15 minutes at 30°. The reaction was stopped with phosphatase inhibitors and analyzed by Western blot.

Phosphoamino acid analysis, tryptic mapping, HPLC fractionation.

501mel cells were starved for 30 minutes in serum-free, phosphate-free RPMI medium, then labeled for 3 hours using 1 mCi/ml $^{32}$p inorganic phosphate. Cells were stimulated with SI or TPA and solubilized in IP buffer. Mi proteins were immunoprecipitated overnight at 4° C., electrophoresed and transferred to nitrocellulose. Bands were cut out and digested 20 hours at 37° with 25 µg TPCK-treated trypsin (SIGMA). Phosphoamino acid analysis and phosphopeptide mapping were carried out as described (Boyle, W., et al., *Methods Enz.* 210, 110-149 (1991)) using pH 8.9 ammonium carbonate. HPLC fractionation utilized a 25 cm C18 reverse phase column (Vydac) and an acetylnitrile gradient (0-70% in 0.1% trifluoracetic acid) at a flow rate of 0.2 ml/minute. Fractions were assayed by Cerenkov counting.

In vitro kinase assay.

Cells were activated and lysed as described and 4 µl of anti-ERK-2 antiserum (Santa Cruz) plus 20 µl of Protein A agarose beads were added to the lysate and mixed at 4° overnight. Beads were washed three times with lysis buffer and once with UVK buffer (50 mM Hepes pH 7.6, 2 mM sodium vanadate, 10 mM magnesium chloride, 1 mM PMSF, 2 mM DTT and 50 µM ATP). For each reaction, 40 µl IVK buffer, 1 µl $\gamma^{32}$p. ATP, and phosphoacceptor protein were added. Myeline basic protein (5 µg) or Mi histidine fusion proteins Taq-Taq, Taq-Sac, or Bam-Bam (Tachibana, M., et al., *Hu. Mol. Genet.* 3, 553-7 (1994)) (4 µl at 0.065 $^{280}$OD) were added as substrates and incubated at 30° C. for 30 minutes. Reactions were stopped by addition of 2×SDS sample buffer and analyzed by Western blot and autoradiography.

Luciferase assay.

The human tyrosinase promoter reporter encompasses nucleotides −300 to +80 (Bentley, N. J., et al., *MoL cell. Biol.* 14, 7996-8006 (1994)) in the pGL2Basic luciferase reporter (Promega). Wild type Mi and the S73A mutant were cloned into the pEF-BOS expression vector (Mizushima, S., et al., *Nucl. Acids Res.* 18, 5322 (1990)). The plasmid encoding constitutively active Raf was the 24G deletion mutant (Stanton, V., et al., *Mol. cell. Biol.* 9, 639-647 (1989)), a gift from Dr. Geoffrey Cooper (Dana-Farber Cancer Institute, Boston, Mass.). Wild type MEK plasmid was a gift from Dr. Len Zon (Children's Hospital, Boston, Mass.). Transfections were performed by adding plasmid DNA (10 μg total for 6 cm plate) to 300 μl DMEM, mixing 1:1 with a 5% lipofectamine/DMEM solution, and incubating at room temperature for one hour. BHK cells maintained in DMEM/10% FCS were washed twice with serum-free DMEM prior to transfection. DNA/lipofectamine was added to 2 ml DMEM on a 6 cm plate. Cells were incubated overnight at 37° and fed the next morning. Assays were harvested 8 hours later and analyzed with a Moonlight 2010 Luminometer using reagents and recommendations of the manufacturer (Analytical Luminescence Laboratory). Luciferase data were normalized to β-galactosidase activity in all samples.

Immunohistochemistry: Mi antibodies were generated against the N-terminus Taq-Sac fragment of human Mi expressed as His-fusion and shown not to cross react with other b-HILH-ZIP factors by DNA mobility shift assay (data not shown).

Cells are grown on glass chamber slides (Fisher Scientific, Pittsburgh, Pa.) and will be fixed with 3% formaldehyde in PBS for 30 minutes and washed followed by 10 minutes in 1% Triton X-100. After another PBS wash, slides will be incubated w/3% $H_2O_2$ to remove endogenous peroxidase. The anti-Mi monoclonal antibody 1:10-1:40 or anti-TFE3 monoclonal antibody (PharMingen, San Diego, Calif.) 1:250-1:500 will be added for 1 hour. The Vecta-stain Elite kit (Vector Laboratories, Burlingame, Calif.) is then used for immunohistochemical staining according to manufacturer's instructions. The diaminobenzidine (DAB) reagent (Vecta Laboratories) is applied for 2-4 minutes and the slides are analyzed under light microscopy. Immunoprecipitation/Western blotting: Immunoblots of melanoma cells are generally preceded by immunoprecipitation which concentrates the antigen and permits efficient on-plate cell lysis in 1% Triton X-100 detergent with 150 mM NaCl, Tris PH 7.6,2 μg/ml aprotinin, 2 μg/ml leupeptin, 200 μg/ml trypsin inhibitor, 500 μg/ml antipain, 10 mM sodium fluoride, 1 mM sodium vanadate, 2 mM phenylmethylsulfonyl fluoride (PMSF), 20 mM sodium pyrophosphate, 10 μg/ml pepstatin. The soluble fraction is incubated for 1-2 hours on ice with appropriate antibodies and washed protein A agarose beads (Gibco-BRL, Gaithersburg, Md.) are added. The mixture is rotated at 4° C. for a minimum of 12 hours. Beads are then washed 3 times with PBS, resuspended in 2% SDS/1% glycerol, boiled for 5 minutes, and eluted proteins are resolved on 8% SDS/polyacrylamide gels (4% SDS/polyacrylamide stacking gel) run at 200 volts for 6-8 hours. Proteins are transferred to nitrocellulose with methanol/glycine electrotransfer (BioRad, Hercules, Calif.). The membrane is blocked in 5% milk for 1 hour at room temperature or overnight at 4° C. After washing in 10 mM Tris pH 7.6, 150 mM NaCl, 0.5% Tween (TBST), 1:40 dilution of the Mi antibody or 1:500 dilution of TFE3 antibody or alpha tubulin 1:500 dilution (Sigma, St. Louis, Mo.) is added for 1 hour at room temperature. After washing, goat-anti-mouse horseradish peroxidase conjugated antibody (Cappel, West Chester, Pa.) is added for 40 minutes. After washing, the enhanced chemiluminescence reaction is performed (Amersham, Arlington Heights, Ill.).

PCR and Southern Analysis of Genomic DNA. Genomic DNA can be extracted form lenanocytes, or mast cells using the PUREGENE™ kit (Gentra Systems, Plymouth, Minn.) according to manufacturer's instructions. The genomic PCR reactions employ 50 ng of purified genomic DNA under the following conditions: 94° C. for 2 minutes, 57° C. for 1 minute and 72° C. for 2 minutes except for exon 9 where an annealing temperature of 60° C. for 1 minute was used for 30 cycles. For Southern analysis, 10 μg of genomic DNA is digested with each of the following restriction enzymes Hinc II, Xba I, and Bam HI using the manufacturer's instructions (New England Biolabs). The digested DNA is electrophoresed on a 1% agarose/TBE gel. The gel is denatured with 0.25 M HCl followed by 0.5 M. NaOH/1.5 M NaCl, and equilibrated with Tris pH 8.0/1.5 M NaCl. The DNA is transferred to nylon membranes, UV crosslined, and prehybridized for 30 minutes with Quik-Hyb (Strategene, LaJolla, Calif.) at 650C. $^{32}$P-dCTP radiolabeled full length Mi cDNA is made using the Strategene prime-it random labeling kit. $10^6$ cpm/ml of Quik-Hyb solution is used and hybridization is performed at 65° C. for 2 hours.

RT-PCRINorthern analysis: Total cellular RNA from a malignant tissue and cultured cells are isolated using RNAzol (Tel-Test, Friendswood, Tex.) according to the manufacturer's instructions. A series of primers, for example, to mouse microphthalmia exons 5, 6, 7, 8 and 9 are synthesized: 5' exon 5 CCGTCTCTGGAAACTTGATCG (SEQ ID NO: 1); 5' exon 6 CGTGTATTTTCCCCACAGAGTC (SEQ ID NO:2); 5' exon 8 GACATGCGGTGGAACAAGGG (SEQ. ID NO:3); 5' exon 9 GAGCTGGAGATGCAGGCTAG (SEQ. ID NO:4); 3' exon 5 GTTGGGAAGGTTGGCTGGAC (SEQ. ID NO:5); 3' exon 6 CTGCCTCTCTTTAGCCAATGC (SEQ. ID NO:6); 3' exon 7 GGATCATTTGACTTGGGGATCAG (SEQ. ID NO:7); 3' exon 8 CTGTACTCTGAGCAGCAGGTG (SEQ. ID NO:8); 3' exon 9 GCTCTCCGGCATGGTGCCGAGG (SEQ. ID NO:9). cDNA are made using the Gibco BRL RT-PCR kit (Grand Isle, N.Y.). 1-5 μg of total RNA are used for each reaction along with 30-100 μmol of 3' primer and 200 units of SuperScript II TM reverse transcriptase and incubated for 50 min at 42° C., 2-4 μl of the 20 μl cDNA reaction mixture is used for PCR reactions which contained: Taq polymerase (Fisher Scientific), dNTP's (Pharmacia Biotech), and PCR buffer (Perkin Elmer) and with incubations at 94° C. for 2 minutes, 57° C. for 1 minute and 72° C. for 2 minutes for 30 cycles (Annealing temperatures for reactions containing 5' exon 6 are 67° C.; for 5' exon 7 was 57° C.; and for 5' exon 8 and 5' exon 9 are 62° C.). 25-50 μl of the 100 μl reaction mixtures are resolved by electrophoresis in non-denaturing 8-0% polyacrylamide gels. Negative controls are performed with water in place of DNA. The RT-PCR product form 5' exon 5 and 3' exon 8 for wild type rat is gel purified and sequenced. The sequence is confirmed from 4 independent PCR reactions. Mi expression is examined using Northern analysis with 20 μg of total RNA loaded on a formaldehyde gel, transferred to nylon membranes, and probed with radiolabeled full length mi DNA for 2 hours at 65° C. in Quick-hyb solution. For loading control, a radiolabeled 500 bp Xba I/Hind III fragment of the human glyceraldehyde 3' phosphate dehydrogenase (GAPCH) is used.

Cell Lines, RT-PCR, and Western blotting: NIH3T3 murine fibroblasts, B16 murine melanoma, and human neuroblastoma lines IMR-32 and SK-N-SH were grown in DMEM with 10% fetal bovine serum (FBS). The human melanoma cell lines (gift of Dr. R. Halaban, Yale University) 501-mel (24), MeWo, and YUZAZ6(36) were grown in Ham's F10 media supplemented with 10% FBS. RT-PCR and Western blotting were carried out as described (37). Primers to the mi gene flanking exons 5-8 were: 5' exon 5 CCCGTCTCTGGAAACTTGATCG (SEQ ID NO:8) and 3' exon 8 CTGTACTCTGAGCAGCAGGTG (SEQ ID NO:10).

Immunofluorescence and immunohistochemistry: Mi monoclonal antibodies (12, 37) failed to crossreact with other b-HLH-Zip factors by immunoprecipitation and DNA mobility shift assay ((37) & data not shown). CS recognizes mouse and human Mi and was used for Western blotting. D5 recognizes human Mi only and was used for immunostaining. For staining, cells (grown on glass chamber slides (Fisher Scientific, Pittsburgh, Pa.)) were fixed with 3% formaldehyde in phosphate buffered saline (PBS) for 30 minutes. D5 antibody (diluted 1:40) was added for 1 hour. The Vecta-stain Elite kit (Vector Laboratories, Burlingame, Calif.) was used for immunohistochemical staining per manufacturer's instructions. The diaminobenzidine reagent (Vector Laboratories) was applied for 2-4 minutes. For immunofluorescence, the Cy-3 conjugated goat anti-mouse (Jackson Immunological) was used. Nuclei were stained with 10 ng/ml DAPI (Sigma). All incubations were followed by three washes with 0.1% Triton X-100 in PBS.

Histopathology: 80 sequential cases of melanoma were selected from the pathology files of Albany Medical Center. Of these, 4 were excluded due to unavailability of adequate lesional tissue. Histopathology was reviewed by two of the authors (RK and MM) to confirm all diagnoses. Immunohistochemical studies were performed utilizing formalin fixed paraffin-embedded tissue. Sections were cut at 4 micrometers, heated at 60° C., deparaffinized in xylenes, and hydrated in a graded series of alcohols. Primary antibodies included rabbit antibody S-100 (Ventana, prediluted), mouse monoclonal antibody HMB-45 (Ventana, prediluted), and monoclonal antibody D5 to Mi (undiluted). Antigen retrieval was performed using microwaving in citrate buffer for Mi antibody. Staining was performed with the Ventana ES automated immunohistochemistry system using the Ventana DAB Detection Kit (Ventana Medical Systems Inc.) Tissues known to express the antigen of interest were used as positive controls whereas removal of the primary antibodies in the test tissues were used as negative controls. Nuclear staining for Mi was regarded as positive whereas cytoplasmic staining alone was considered negative (observed in two breast carcinomas, see below). S-100 antibody staining was considered positive if cytoplasmic staining was present and, for HMB-45, cytoplasmic staining was considered positive. In addition, 9 cases of desmoplastic/neurotropic melanoma and 2 cases of pure spindle cell melanoma (not from the consecutive series) were examined with the same antibodies. 81 non-melanocytic tumors (detailed below) were selected to test the specificity of Mi and HMB-45, and selected melanocytic and non-melanocytic skin lesions (detailed below) were also stained for Mi.

Results

Figure 1B:
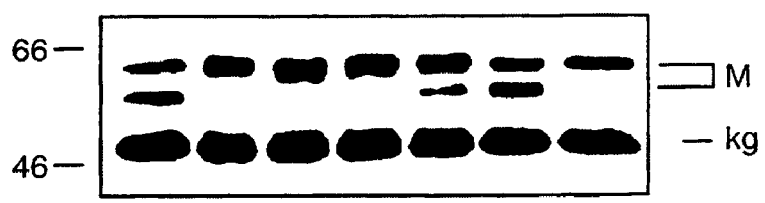

Western blot analysis of a human melanoma cell line revealed two Mi species with relative mobilities of 54 and 60 kd. Activation of c-Kit by SI completely shifted the lower band to the position of the upper band (FIG. 1A). This shift occurred rapidly but transiently; the lower band reappeared within two hours. A smaller but sustained shift was induced when cells were treated with phorbol ester (TPA), a potent activator of protein kinase C. As detected by phosphotyrosine antibodies, treatment with SI but not TPA led to the expected phosphorylation of c-Kit (FIG. 1A). Both stimuli resulted in the activation of MAP kinase, which correlated temporally with the shift in Mi protein (FIG. 1A). In vitro phosphatase treatment resulted in a discrete, dose-dependent shift of the upper form of Mi to the faster-migrating species (FIG. 1B). This shift was blocked by phosphatase inhibitors, suggesting that the mobility change observed in cell extracts was due to phosphorylation.

Figure 2A:
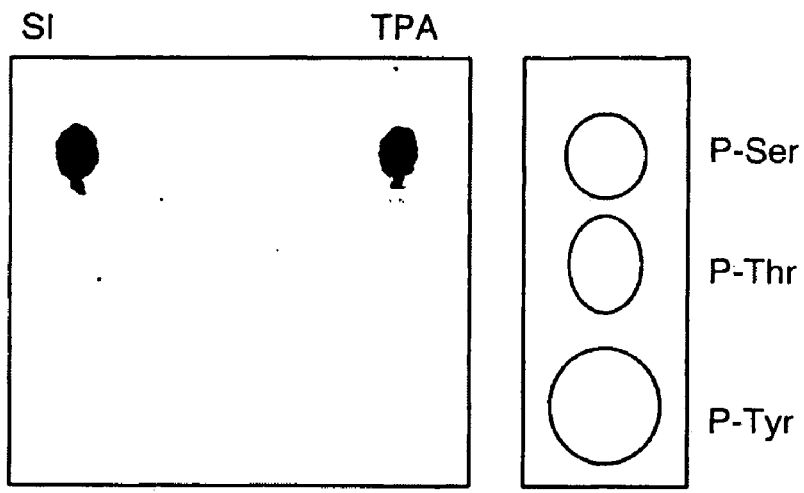
FIGS. 2A and 2B show serine phosphorylation of Mi is prevented by MEK inhibition.

In vivo labeling of the Mi proteins with $^{32}$P-orthophosphate indicated that both Mi forms were phosphoproteins (see below). Phosphoamino acid analysis revealed phosphoserine, but no detectable phosphotyrosine or phosphothreonine (FIG. 2A), a finding consistent with the failure of anti-phosphotyrosine antibodies to detect Mi in total cell extracts (not shown). These results indicated that c-Kit was not responsible for directly phosphorylating Mi, and therefore attention was focused on downstream kinases.

Figure 2B:
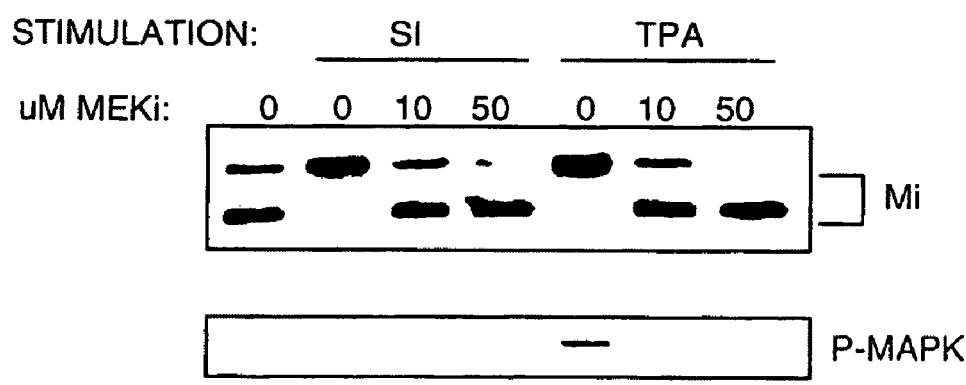

Phosphotyrosine blotting showed that MAP kinase activation correlated with Mi phosphorylation in cells (FIG. 1A). One family of MAPKs activated by the c-Kit signaling cascade includes ERK-1 and ERK-2 (Okuda, K., et al., Blood 79, 2880-7 (1992)) which translocate to the nucleus upon activation and phosphorylate a number of transcription factors (Marshall, C., Curr. Opin. Cell 80, 179-15 (1995); Treisman, R., Curr. Opin. Cell Biol. 8, 205-215 (1996)). The ERKs are activated by a dual phosphorylation event carried out by the upstream kinase MEK-1 (Ahn, N., et al., Curr. Opin. Cell Biol. 4, 992-999 (1992)). We examined the effect of a specific inhibitor of MEK activity, PD98059 (MEKi), on the phosphorylation of Mi in uivo. As shown in FIG. 2B, MEKi prevented ERK phosphorylation and caused a dose-dependent inhibition of the Mi mobility shift stimulated by both SI and TPA. MEKi did not affect the tyrosine phosphorylation of c-Kit in response to SI, indicating that the drug did not grossly perturb signaling (not shown). These results suggested that Mi might be a substrate for activated ERK in vivo.

Figure 3A:
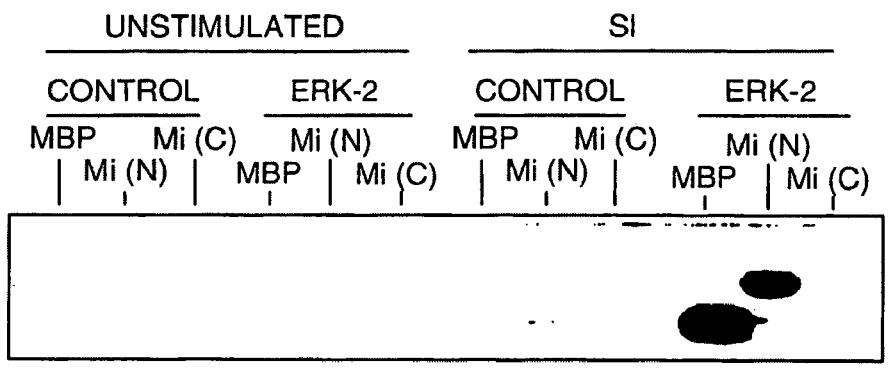

The ability of ERKs to phosphorylate Mi was tested in vitro using immunoprecipitated kinase. ERK-2 strongly phosphorylated an amino-terminal fragment of Mi but failed to phosphorylate a large fragment from the carboxy terminus (FIG. 3A). This in vitro phosphorylation was dependent upon prior activation of the cells with SI (FIG. 3A). Jun N-terminal kinase and p38 kinase did not reveal detectable c-Kit-dependent kinase activity on recombinant Mi proteins (not shown). ERK-1 was not significantly expressed in the cells (not shown). Thus c-Kit stimulation generated activated ERK-2 capable of phosphorylating Mi in vitro.

Figure 3B:
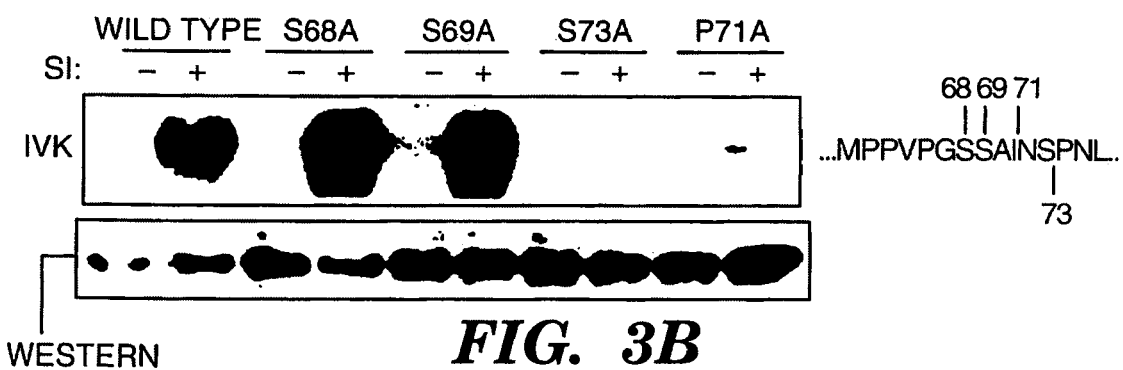

The amino-terminal region of Mi contains three closely spaced serine residues that could potentially act as MAPK phosphoacceptor sites (FIG. 3B). Mutation of the two upstream serines (S68 and S69) had no effect on in vitro phosphorylation by ERK-2, while mutation of serine 73 completely abolished in uitro phosphorylation (FIG. 3B).

Mutation of proline 71, which would contribute to a S73-directed consensus MAPK site (PXSP) resulted in a severe reduction of ERK-2 phosphorylation (FIG. 3B).

To determine whether ERK-2 was the kinase responsible for Mi phosphorylation in vivo, we carried out two-dimensional phosphopeptide mapping and high pressure liquid chromatography (HPLC) fractionation of the trypsin-digested $^{32}$P-labeled Mi doublet. The patterns derived from both Mi bands contain peptides representing constitutive phosphorylations (FIG. 3C, compare Lower vs. Upper). However, a unique phosphotryptc fragment appears in the map of the upper Mi band, which corresponds to the c-Kit-dependent phosphorylation (FIG. 3C, Upper). A comparison of this spot to that generated from in vitro ERK-2 phosphorylated recombinant Mi showed identical two-dimensional migration (FIG. 3C, Upper vs. Recombinant). HPLC fractionation of tryptic digests from in vivo or in vitro phosphorylated protein confirmed that they contain a single major co-eluting phosphotryptic fragment (FIG. 3D). The second labeled peak eluting from both HPLC fractionations likely results from oxidative peptide bond cleavage resulting from performic acid treatment (Boyle, W., et al., *Methods Enz.* 210, 110-149 (1991)).

The site-directed Mi mutant S73A failed to undergo TPA-induced mobility shift in transfected cells (FIG. 3E) indicating that phosphorylation of S73 is most likely responsible for the Kit-dependent mobility shift. The tryptic maps, HPLC fractionation, and in vitro kinase data strongly suggest that ERK-2 is activated by the c-Kit signaling cascade and subsequently phosphorylates Mi at S73.

Figure 4A:
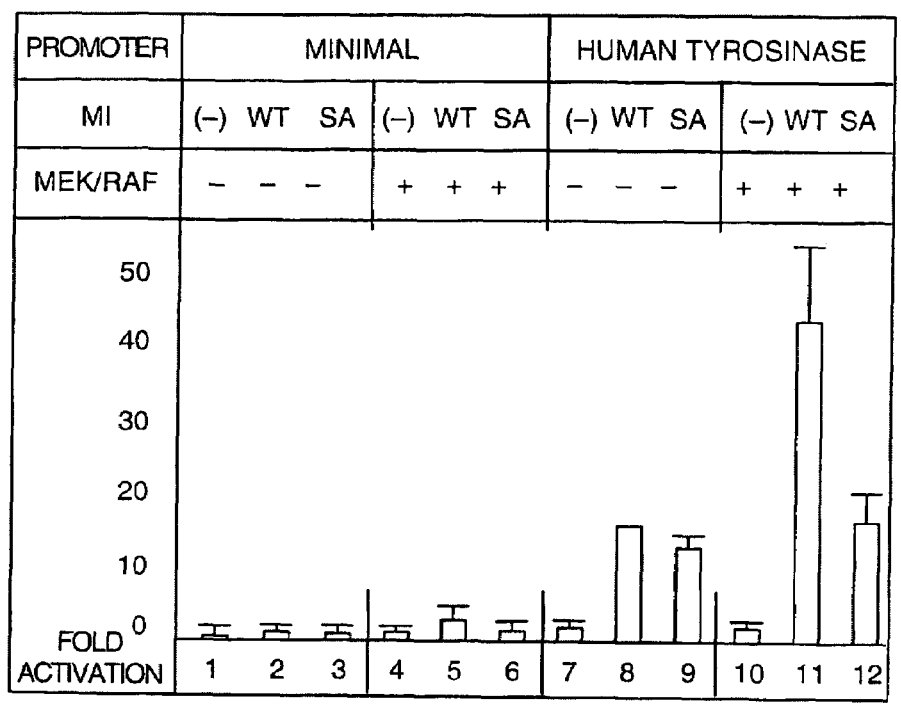
FIGS. 4A and 4B show MAPK phosphorylation enhances Mi-dependent transactivation.

The impact of MAPK phosphorylation of Mi on its ability to transactivate was tested on a luciferase reporter driven by the tyrosinase promoter, a rate limiting enzyme in the pigmentation response (Hearing, V., et al., *J. Biochem,* 19, 1141-1147 (1987)). Mi has been shown to transactivate this promoter through M box enhancer elements (conserved in the promoters of all known pigment enzyme genes) (Hemesath, T. J., et. al., *Genes Deu.* 8, 2770-80 (1994); Bentley, N. J., et al., *Mol. cell. Biol.* 14, 7996-8006 (1994); Yasumoto, K., et al., *Mol. Cell Biol.* 14, 8058-70 (1994)). Due to the transient nature of Kit signals (see FIG. 1), constitutively active Raf plus wild type MEK were used to achieve sustained activation of the MAP kinase pathway and permit measurable accumulation of luciferase. Co-transfection of Raf/MEK resulted in up-regulation of tyrosinase reporter activity in the presence of wild type Mi (FIG. 4). Mutant S73A showed no significant transcriptional enhancement in response to Raf/MEK despite expression levels comparable to those of wild type Mi (data not shown, see FIG. 3E). Thus MAPK phosphorylation at serine 73 mediates up-regulation of Mi transcriptional activity.

Figure 4B:
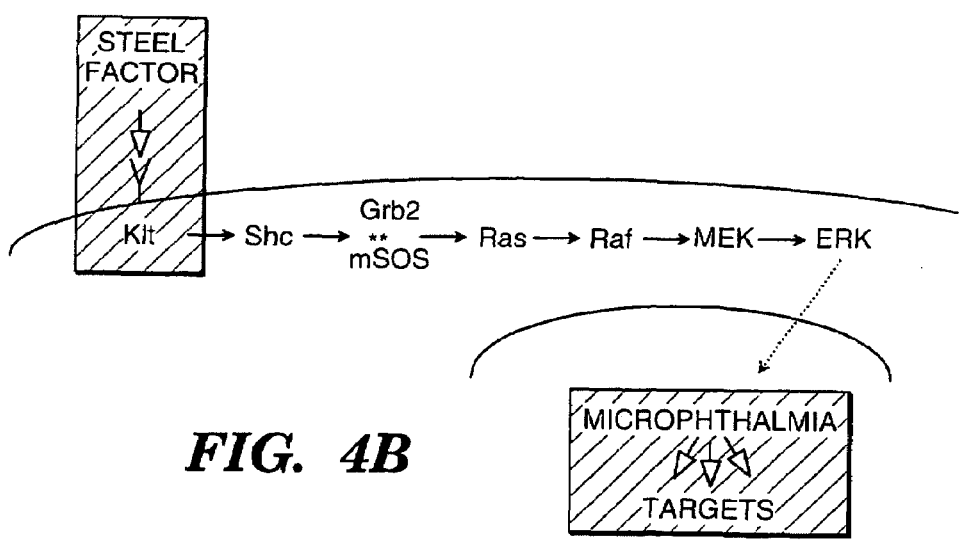

The phosphorylation of Mi in response to c-Kit activation identifies a nuclear target that may underlie the well-documented phenotypic overlap between mice bearing mutations in SI, Kit and Mi. It is likely that the specificity of the MAPK pathway between Kit and Mi lies in the highly restricted temporal and spatial expression of SI, Kit and Mi in vivo. Mi/Kit signaling illustrates use of general signaling machinery to link an individual cytokine to a specific transcription factor (FIG. 4B). These results are consistent with a recent report that subcutaneous SI induces localized pigmentation in humans (Costa, J., et al., *J. Fxp. Med* 183, 2681-2686 (1996)). cAMP elevation may also up-regulate the tyrosinase promoter in a manner involving Mi via signals originating from the melanocyte stimulating hormone receptor (Englaro, W., et al., *J. biol. Chem.* 270, 24315-24320 (1995); Bertolotto, C., et al., *J. Cell Biol* 134, 747-755 (1996)).

Interestingly, mast cells from mi mutant mice underexpress c-Kit (Ebi, Y., et al., *Blood* 80, 1454-62 (1992)) and Mi may upregulate c-Kit expression from a binding site in the c-Kit promoter (Tsujimura, T., et al., *Blood* 88, 1225-33 (1996)). Additionally, Bernstein and colleagues found that transfection of the c-Kit related CSF-1 receptor restores cytoline-responsiveness to kit-mutant but not mi-mutant mast cells (Okuda, K., et al., *Blood* 79, 2880-7 (1992)), consistent with the role proposed here for Mi as a downstream target of cytokine-initiated MAPK signals. Moreover, genetic experiments (Paulson, R., et al., *Nature Genet.* 13, 309-315 (1996); Lorenz, U., et al., *J. Exp. Med.* 184, 111-1126 (1997)) demonstrated that germline deficiency of the phosphatase SHP1 (a negative regulator of Kit signaling) enhances SI-induced MAP kinase activation and partially rescues the number of resident mast cells. Kit-stimulated MAPK activation and Mi phosphorylation may alter expression of genes controlling cell lineage commitment, development or survival.

Figure 5A:
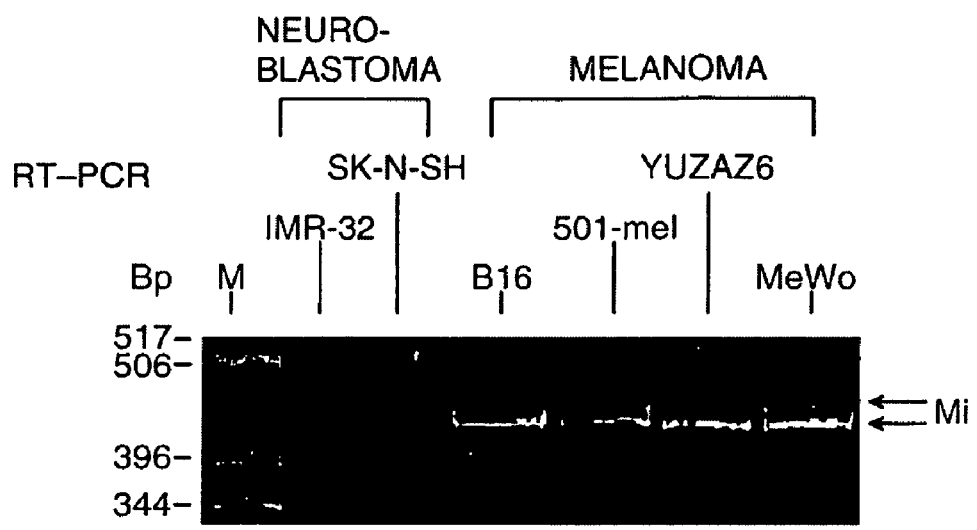
FIGS. 5A-C show identification of human Mi.
Figure 5B:
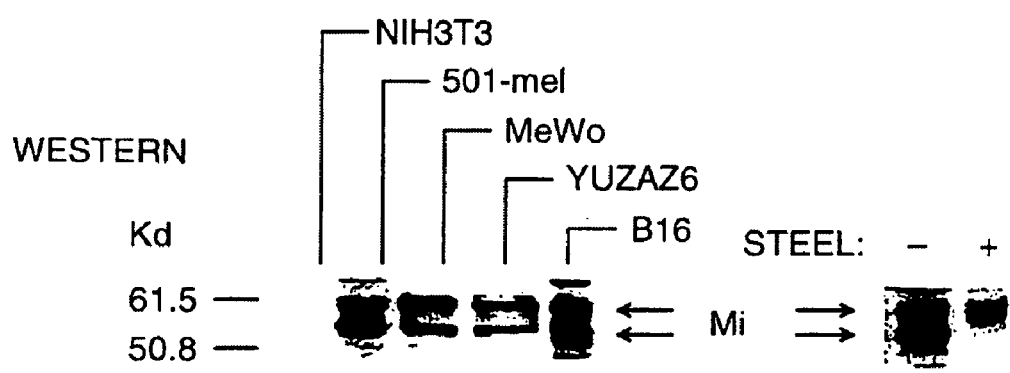
Figure 5C:
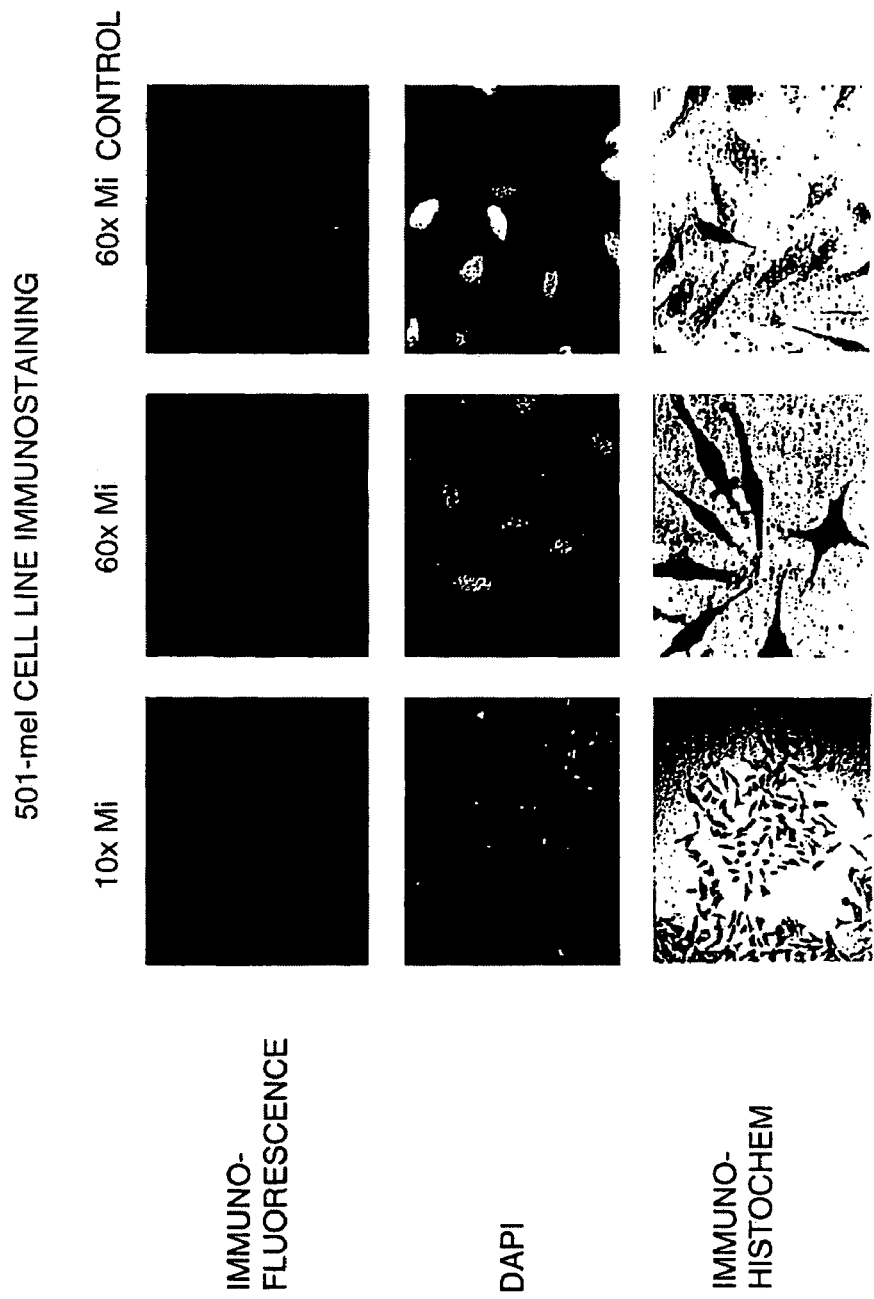

Using reverse transcriptase PCR, bands corresponding to Mi were identified in a series of five melanoma cell lines, four human (24, 36) and one murine. A doublet representing the alternative splice of an 18 bp segment (4) was observed in each case (FIG. 5A) and verified by sequencing. Two human neuroblastoma cell lines, also neural crest derived tumors, failed to produce Mi-specific PCR products (FIG. 5A). Western blot analysis of 501-mel melanoma cell line extracts (FIG. 5A, lanes 2-5) revealed Mi-specific bands as a doublet migrating at ~52 and 56 kd. Biochemical analyses have confirmed the identity of these Mi bands and determined that these isoforms differ in the presence of a MAP kinase-mediated phosphorylation at serine 73 in the upper migrating species (12). A fibroblast extract (FIG. 5B, lane 1) lacked the Mi protein bands. In addition, Steel factor (c-Kit ligand) triggered a mobility shift from the lower to the upper migrating form as preciously described (FIG. 6B lanes 6 & 7, (12)). Direct staining of melanoma cells for Mi revealed nuclear signal by immunofluorescence and immunohistochemistry (FIG. 5C). Two color fluorescence with DAPI identifies nuclei in the same samples (FIG. 5C). Thus, Mi is expressed in nuclei of these melanoma cells.

Figure 6:
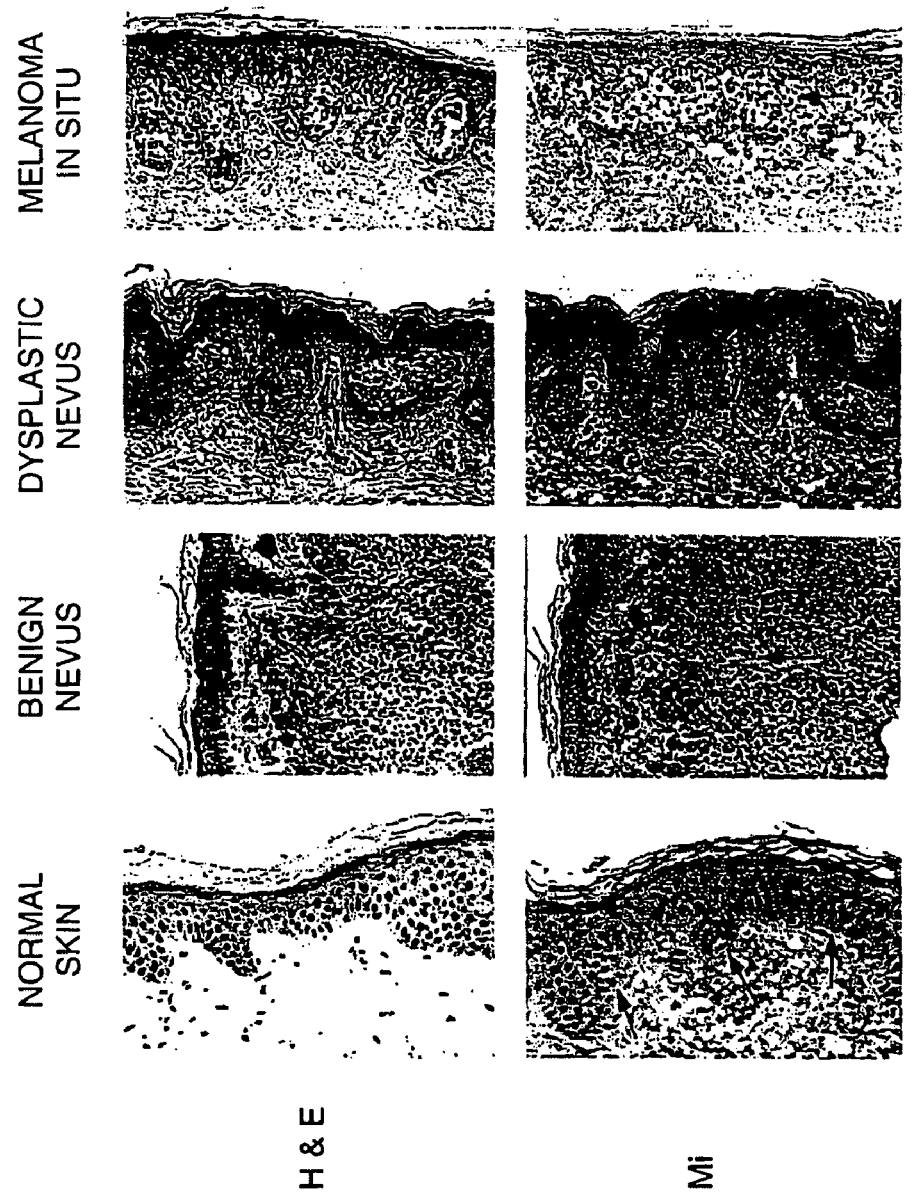
FIG. 6 shows immunohistochemical staining of Normal skin with Hematoxylin and Eosin (H&E) and Microphthalmia (Mi) antibody shows Mi nuclear staining of melanocytes at the epidermal/dermal border. Benign Nevus, Dysplastic Nevus and Melanoma In situ show Mi staining in the melanocytic component of these lesions. Arrows indicate areas of Mi positive staining. Asterix indicates endogenous melanin pigment.

Expression of Mi was next tested by immunohistochemical staining in normal skin, nevi, dysplastic nevi, and melanomas. Paraffin-embedded tissue samples were stained with Mi and counterstained with hematoxylin. Control samples from each section were separately stained with hematoxylin and eosin (H & E) for comparison. Within normal skin, the Mi specific antibody highlighted nuclear staining within individual melanocytes (FIG. 6, see arrows). In addition, melanocytes in 9 benign nevi and 4 dysplastic nevi were all positive for Mi (representative cases shown in FIG. 6).

Mi expression was tested in a series of consecutively accessioned human pathologic melanoma specimens. Of the 76 cases, 19 were melanomas in situ, 50 were conventional melanomas, and 7 were metastatic melanomas. Eight cases were histologically amelanotic. Nine cases had a predominantly spindled cell morphology, eight cases a mixed spindled/epithelioid morphology, and the remainder a predominantly epithelioid morphology.

Figure 7:
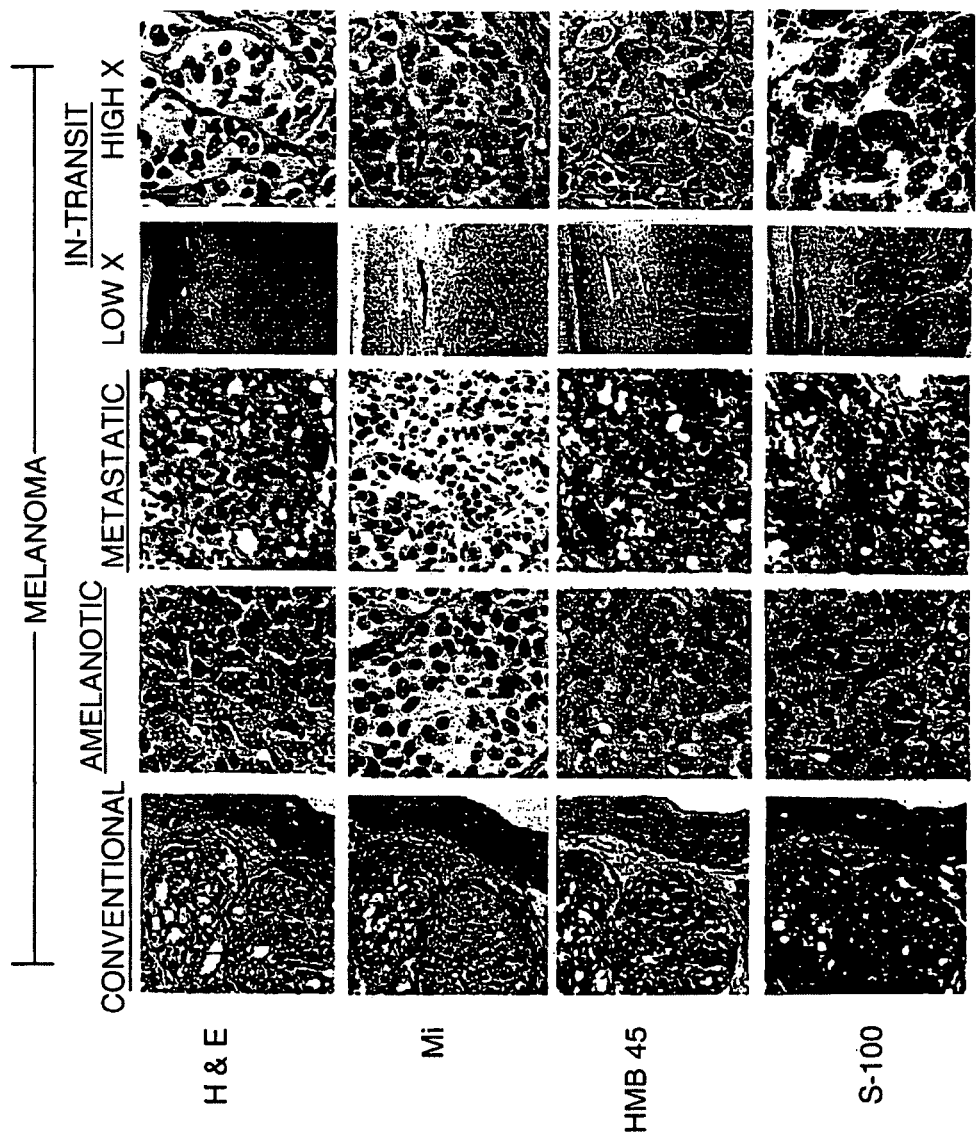
FIG. 7 shows immunohistochemistry of melanomas. Conventional melanoma represents a primary melanoma (epidermis and dermis shown at 40× power) stained with Hematoxylin and Eosin (H&E), Microphthalmia (Mi), HMB-45 and S-100. Amelanotic (unpigmented) melanoma is shown at 60×. Metastatic refers to melanoma within a lymph node (60×). In Transit refers to primary melanoma with deep dermal invasion without contiguous epidermal involvement, at low (10×) and high power (60×).
Figure 8A:
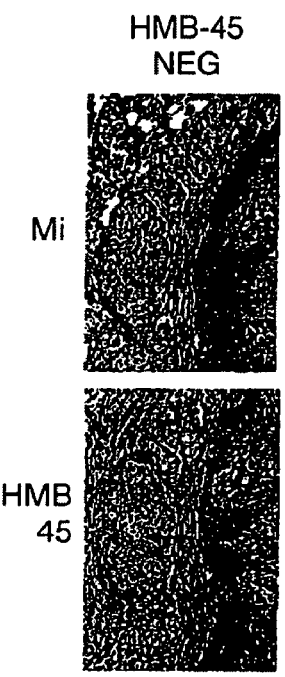
FIG. 8 shows Mi staining of S-100 negative and HMB-45 negative melanomas. HMB-45 neg refers to a conventional melanoma that was negative for HMB-45 but positive for Mi (arrow). HMB-45 in situ-selective is a case where HMB-45 was positive within the in situ component (small arrow), but not the invasive melanoma component ("invasive") while Mi stained both in situ (small arrow) and invasive components. S-100 neg refers to case where Mi was positive, but HMB-45 and S-100 were negative. Deep staining refers to a case where anti-Mi identified melanoma nests deep in the dermis (circled), not easily appreciated by H&E or HMB-45.
Figure 8B:
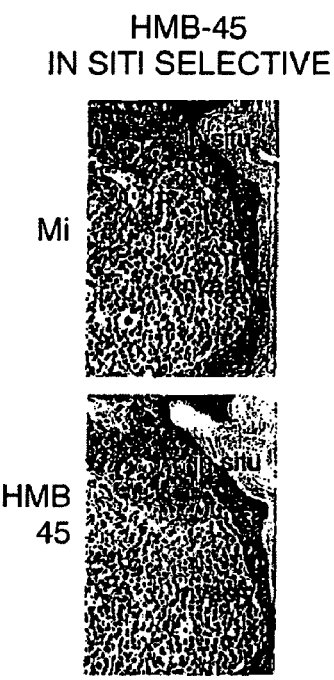
Figure 8C:
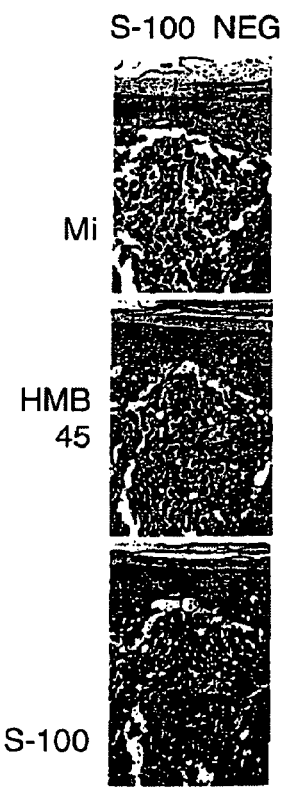
Figure 8D:
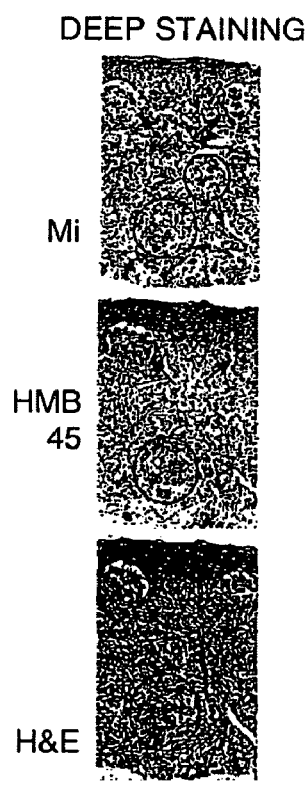

Mi expression was positive and nuclear in all 19 melanomas in situ (Table 1, and FIG. 6). Among the conventional invasive melanomas, Mi was also positive in all cases, again displaying a nuclear staining pattern (Table 1). For the consecutive series, Mi staining was compared in side-by-side fashion with HMB-45 and S-100. The nuclear staining pattern of Mi contrasted the cytoplasmic or more diffuse staining patterns of S-100 and HMB-45 (FIG. 7). All three stains were positive in the majority of cases (Table 1). However, HMB-45 failed to stain 7 cases and produced only rare scattered immunopositivity in 2 more. While known to be less specific for melanoma (31), S100 was positive in all but 5 melanoma cases. Mi staining was positive in all 76 tumors with 2 cases demonstrating focal positivity. FIG. 7 shows representative staining for Mi, HMB-45, and S100 in conventional, amelanotic, metastatic, and in-transit melanomas. The nuclear staining pattern of Mi is compared at low and high powers. The amelanotic tumor happened also to be negative for HMB-45, but was positive for Mi and S-100 (FIG. 7). Mi also stained positively in a melanoma-in-transit (FIG. 7). This invasive tumor resides in the dermal/subdermal region without contiguous extension from overlying epidermis.

Several specific clinical scenarios are shown in FIG. 8, which highlight instances in which Mi can display particular diagnostic utility. An HMB-45 negative melanoma is shown (FIG. 8, column 1) in which nuclear staining for Mi is observed. Another tumor was HMB-45 positive only in the in-situ component (FIG. 8, column 2, arrow), but HMB-45 negative within the invasive component (FIG. 8, column 2 labeled invasive). In contrast, Mi staining was positive in both the in situ and invasive components of this tumor (FIG. 8, column 2). One of the S-100 negative tumors is also shown (FIG. 8, column 3) which also was negative for HMB-45. It, too, stained positively for Mi. Finally, a melanoma is shown in which the Mi stain permitted detection of invasive tumor cell clusters deep within the sample, which might otherwise have been missed (FIG. 8, column 4, see arrow).

Rare variants of melanoma were evaluated for Mi staining. These variants represent <1% of melanomas and were not seen in the consecutive series of 76 melanomas presented. Two pure spindle cell melanomas were stained for S-100, HMB-45, and Mi. One was positive for all three markers, and the other was HMB-45 negative, but positive for Mi and S-100. Nine cases of desmoplastic/neurotropic melanoma were also stained with the 3 markers. All were negative for both Mi and HMB-45, but positive for S-100. Thus while Mi was positive in 100% of melanomas in the consecutive series, like HMB-45 it failed to detect 9 of 9 desmoplastic/neurotropic melanomas.

To assess the specificity of Mi expression among non-melanoma tumors, 81 non-melanocytic tumors were stained for Mi (Table 1). These samples comprised 10 invasive ductal carcinomas of the breast, 10 squamous cell carcinomas of the lung, 10 endometrial adenocarcinomas, 10 thyroid carcinomas, 10 vulvar squamous cell carcinomas, 10 testicular carcinomas, 4 schwannomas, 2 neurofibromas, 1 microcystic adnexal carcinoma, and non-melanoma skin tumors (4 basal cell carcinomas, 4 squamous cell carcinomas, 4 atypical fibroxanthomas, 2 granular cell tumors). Of these tumors, all were negative for Mi nuclear staining, but two breast carcinomas displayed a cytoplasmic staining pattern. Only one thyroid carcinoma displayed focal HMB-45 staining, with the remaining cases being HMB-45 negative. Thus Mi stained cytoplasmic in 2 of 81 non-melanomas, but no cases exhibited nuclear staining.

Table 1: Staining characteristics in 76 consecutive melanomas, rare variants, non-melanoma tumors, and non-melanoma skin tumors. Number of positive cases is given in the numerator and total number of cases in the denominator. Parentheses give percent positive cases. Asterisk indicates that 2 of the 10 breast cancer cases showed cytoplasmic staining for Mi, but were scored negative due to lack of nuclear staining.

TABLE 1

| | Mi + (% positive) | HMB-45 + (% positive) | S-100 + (% positive) |
|---|---|---|---|
| Consecutive series of Melanomas | | | |
| Melanoma in situ | 19/19 (100) | 19/19 (100) | 17/19 (89) |
| Melanoma | 50/50 (100) | 44/50 (88) | 48/50 (96) |
| Amelanotic melanoma | 8/8 (100) | 7/8 (88) | 7/8 (88) |
| Metastatic Melanoma | 7/7 (100) | 6/7 (86) | 6/7 (88) |
| All melanomas in series | 76/76 (100) | 69/76 (91) | 71/76 (93) |
| Rare variants of Melanoma | | | |
| Desmoplastic/neurotropic | 0/9 (0) | 0/9 (0) | 9/9 (100) |
| Pure spindle cell melanoma | 2/2 (100) | 1/2 (50) | 2/2 (100) |
| Non-Melanoma tumors | | | |
| Invasive Ductal Breast Carcinoma | 0/10* (0) | 0/10 (0) | |
| Squamous Carcinoma Lung | 0/10 (0) | 0/10 (0) | |
| Endometrial adenocarcinoma | 0/10 (0) | 0/10 (0) | |
| Thyroid Carcinoma | 0/10 (0) | 1/10 (10) | |
| Squamous Carcinoma Vulva | 0/10 (0) | 0/10 (0) | |
| Testicular Cancer | 0/10 (0) | 0/10 (0) | |
| Schwannoma | 0/4 (0) | | |
| Microcystic Adenexal Carcinoma | 0/1 (0) | | |
| Neurofibroma | 0/2 (0) | | |
| Non-melanoma Skin tumors | | | |
| Basal Cell Carcinoma | 0/4 | | |
| Squamous Carcinoma Skin | 0/4 | | |
| Atypical Fibroxanthomas | 0/4 | | |
| Granular Cell tumors | 0/2 | | |
| All non-melanomas in series | 0/81 (0) | 1/60 (2) | |

In this series of 76 consecutively accessioned melanomas the Mi antibody detected 100% of cases. S-100 and HMB-45 failed to detect 5 and 7 cases respectively of the 76 melanomas. Mi also identified an area of deep dermal staining on a specimen that was difficult to visualize with H&E and negative with HMB-45 staining. This deep staining may confer a worse prognosis because it would alter the measured thickness of the tumor and thereby alter treatment decisions such as optimal surgical margins and/or adjuvant therapy. Mi is also a very specific antibody, staining nuclei in none of 81 non-melanomas, though staining cytoplasms in 2. In this series, compared to current standard markers of melanoma, Mi is more specific than S-100 and is as sensitive, if not more, than HMB-45.

REFERENCES

1. Silver, W. K. (1979) *The coat colors of mice: a model for mammalian gene action and interaction*. (Spinger-Verlag, Incorporated, New York).
2. Hughes, A. E., Newton, V. E., Liu, X. Z. & Read, A. P. (1994) *Nat Genet* 7, 509-12.
3. Tassabehji, M., Newton, V. E. & Read, A. P. (1994) *Nat Genet*. 8, 251-5.
4. Hodgkinson, C. A., Moore, K. J., Nakayama, A., Steingrimsson, E., Copeland, N. G., Jenkins, N. A. & Arnheiter, H. (1993) *Cell* 74, 395-404.
5. Hemesath, T. J., Steingrimsson, E., McGill, G., Hansen, M. J., Vaught, J., Hodgkinson, C. A., Arnheiter, H., Copeland, N. G., Jenkins, N. A. & Fisher, D. E. (1994) *Genes Dev.* 8, 2770-80.

6. Yasumoto, K., Yokoyama, K., Shibata, K., Tomita, Y. & Shibahara, S. (1994) *Mol. Cell. Biol.* 14, 8058-70.
7. Bentley, N. J., Eisen, T. & Goding, C. R. (1994) *Mol. Cell. Biol.* 14, 7996-8006.
8. Bertolotto, C., Abbe, P., Hemesath, T. J., Bille, K., Fisher, D. E., Ortonne, J.-P. & Ballotti, R. (1998) *J. Cell Biol.* 142, 827-35.
9. Price, E. R., Horstmann, M. A., Wells, A., Weilbacher, K. N., Takemoto, C. M., Landis, M. W. & Fisher, D. E. submitted.
10. Lerner, A. B., Shiohara, T., Boissy, R. E., Jacobson, K. A., Lamoreux, M. L. & Moellmann, G. E. (1986) *J. Inuest. Derrnatol.* 87, 299-304.
11. Steingrimsson, E., Moore, K. J., Lamoreux, M. L., Ferre, D. A. A. R., Burley, S. K., Zimring, D. C., Skow, L. C., Hodgkinson, C. A., Arnheiter, H., Copeland, N. G. & et al. (1994) *Nat. Genet.* 8, 256-63.
12. Hemesath, T. J., Price, E. R., Takemoto, C., Badalian, T. & Fisher, D. E. (1998) *Nature* 391, 298-301.
13. Price, E. R., Horstmann, M. A., Wells, A. G., Weilbacher, K. N., Takemoto, C. M., Landis, M. W. & Fisher, D. E. (1998) *J. Biol. Chem.* In Press.
14. Sato, S., Roberts, K., Gambino, G., Cook, A., Kouzarides, T. & Goding, C. R. (1997) *Oncogene* 14, 3083-92.
15. Halaban, R., Bohm, M., Dotto, P., Moellmann, G., Cheng, E. & Zhang, Y. (1996) *J. Invest Dermatol* 106, 1266-72.
16. Barth, A., Wanek, L. A. & Morton, D. L. (1995) *J. Am. Coll. Surg.* 181, 193.
17. Evans, G. R. D. & Manson, P. N. (1994) *J. Am/Coll. Surg.* 178, 523.
18. DeVita, V., Hellman, S. & Rosenberg, S. (1993) *Cancer: Principles and Practice of Oncolgoy* (J.B. Lippincott Company, Philadelphia).
19. Chang, P. & Knapper, W. (1982) *Cancer* 49, 1106-1111.
20. Jonk, A., Kroon, B., Rumke, P., Mooi, W., Hart, A. & Van Dongen, J. (1990) *Br J Surg* 77, 665-8.
21. Reintgen, D., McCarty, K., Woodard, B., Cox, E. & Seigler, H. (1983) *Surg, Gynecol& Obstet* 156, 335-40.
22. Schlagenhauff, B., Stroebel, W., Ellwanger, U., Meier, F., Zimmermann, C., Breuninger, C., Rassner, G. & Garbe, C. (1997) *Cancer* 80, 60-5.
23. Kaufmann, O., Koch, S., Burghard, J., Audring, H. & Dietel, M. (11998) *Mod Pathol* 11, 740-746.
24. Zakut, R., Perlis, R., Eliyahu, S., Yarden, Y., Givol, D., Lyman, S. & Halaban, R. (1993) *Oncogene* 8, 2221-2229.
25. Halaban, R., Cheng, E., Zhang, Y., Moellmann, G., Hanlon, D., Michalak, M., Setaluri, V. & Hebert, D. N. (1997) *Proc Natl Acad Sci USA* 94, 6210-5.
26. Montone K. T., van Belle, P. Elenitsas R., & Elder, D. E. (1997) *Mod Pathol* 10(9):939-44.
27. Rossi, C., Foletto, A., Vecchiato, S., Alessio, N., Menin, N. & Lise, M. (1997) *Eur J Cancer* 33, 2302-12.
28. Cochran, A. & Wen, D. (1985) *Pathology* 17, 340-345.
29. Orchard, G. & Jones, E. (1994) *Britis Journal of Biomedical Science* 51, 44-56.
30. Bacchi, C., Bonetti, F., Pea, M., Martignoni, G. & Gown, A. (1996) *Applied Immunhistochemistry* 4, 73-85.
31. Kahn, H., Marks, A., Thom, H. & Baumal, R. (1983) *Am J Clin Pathol* 79, 341-347.
32. Busam, K., Chen, Y., Old, L., Stockert, E., Iversen, K., Coplan, K., Rosai, J., Barnhill, R. & Jungbluth, A. (1998) *Am J Surg Pathol* 22, 976-982.
33. Elenitsas, R. & Schuchter, L. (1998) *Current opinion in oncology* 10, 162-169.
34. Skelton, H., Maceira, J., Smith, K., McCarthy, W., Lupton, G. & Graham, J. (1997) *Am J Dermatopathol* 19, 580-4.
35. Gown, A., Vogel, A., Hoak, A., Gough, F. & NcNutt, M. (1986) *Am J Pathol* 123, 195-203.
36. Cohen, T., Gitay-Gorey, H., Sharon, R., Shibuya, M., Halaban, R., Levi, B. & Neufeld, G. (1995) *J Biol Chem* 270, 1132-11326.
37. Weilbaecher, K. N., Hershey, C. L., Takemoto, C. M., Horstmann, M. A., Hemesath, T. J., Tashjian, A. H. & Fisher, D. E. (1998) *J Ecp Med* 187, 775-85.
38. Ackerman, L. (1953) *Surgical Pathology* (Mosby, St. Louis).
39. Schmitt, F. & Bachhi, C. (1989) *Histopathology* 15, 281-8.
40. Stefansson, K., Wollmann, R. & Jerkovic, M. (1982) *Am J Pathol* 106, 261-8.
41. Guillermo, A., Herrera, E., Turbat-Herrera, A. & al., e. (1988) *Am J Clin Pathol* 89, 168-76.
42. Drier, J., Swanson, P., Cherwitz, D. & Wick, M. (1987) *Arch Pathol Lab Med* 111, 447-52.
43. Zarbo, R., Gown, A., Visscher, D. & Crissman, J. (1990) *Mod. Pathol.* 3, 494-501.
44. Yoneda, T., Sasaki, A. & Mundy, G. (1994) *Breast Cancer Research and Treatment* 32, 73-84.
45. Scher, H. & Yagoda, A. (1987) *American J Medicine* 82, 6-28.
46. Littlewood-Evans, A., Bilbe, G., Bowler, W., Farley, D., Wlordski, B., Kokubo, T., Inaoka, T., Sloane, J., Evans, D. & Gallager, J. (1997) *Cancer Research* 57, 5386-90.
47. Carlson, J., Dickerson, G. & Sober, H. (1995) *Cancer* 75, 478.
48. Labrecque, P., Hu, C. & Winkelmann, R. (1976) *Cancer* 38, 1205-13.
49. DiMaio, S. M., Mackay, B., Smith, J. L. J. & Dickersin, G. R. (1982) *Cancer* 50, 2345-54.
50. Weiss & Enzinger (1983), pp. 919-921.

The references described herein are incorporated herein by reference.

33. Elenitsas, R. & Schuchter, L. (1998) *Current opinion in oncology* 10, 162-169.
34. Skelton, H., Maceira, J., Smith, K., McCarthy, W., Lupton, G. & Graham, J. (1997) *Am J Dermatopathol* 19, 580-4.
35. Gown, A., Vogel, A., Hoak, A., Gough, F. & NcNutt, M. (1986) *Am J Pathol* 123, 195-203.
36. Cohen, T., Gitay-Gorey, H., Sharon, R., Shibuya, M., Halaban, R., Levi, B. & Neufeld, G. (1995) *J Biol Chem* 270, 1132-11326.
37. Weilbaecher, K. N., Hershey, C. L., Takemoto, C. M., Horstmann, M. A., Hemesath, T. J., Tashjian, A. H. & Fisher, D. E. (1998) *J Ep Med* 187, 775-85.
38. Ackerman, L. (1953) *Surgical Pathology* (Mosby, St. Louis).
39. Schmitt, F. & Bachhi, C. (1989) *Histopathology* 15, 281-8.
40. Stefansson, K., Wollmann, R. & Jerkovic, M. (1982) *Am J Pathol* 106, 261-8.
41. Guillermo, A., Herrera, E., Turbat-Herrera, A. & al., e. (1988) *Am J Clin Pathol* 89, 168-76.
42. Drier, J., Swanson, P., Cherwitz, D. & Wick, M. (1987) *Arch Pathol Lab Med* 111, 447-52.
43. Zarbo, R., Gown, A., Visscher, D. & Crissman, J. (1990) *Mod. Pathol.* 3, 494-501.
44. Yoneda, T., Sasaki, A. & Mundy, G. (1994) *Breast Cancer Research and Treatment* 32, 73-84.

45. Scher, H. & Yagoda, A. (1987) *American J Medicine* 82, 6-28.
46. Littlewood-Evans, A., Bilbe, G., Bowler, W., Farley, D., Wlordski, B., Kokubo, T., Inaoka, T., Sloane, J., Evans, D. & Gallager, J. (1997) *Cancer Research* 57, 5386-90.
47. Carlson, J., Dickerson, G. & Sober, H. (1995) *Cancer* 75, 478.
48. Labrecque, P., Hu, C. & Winkelmann, R. (1976) *Cancer* 38, 1205-13.
49. DiMaio, S. M., Mackay, B., Smith, J. L. J. & Dickersin, G. R. (1982) *Cancer* 50, 2345-54.
50. Weiss & Enzinger (1983), pp. 919-921.

The references described herein are incorporated herein by reference.

What is claimed is:

1. A method for screening for melanoma using immunohistochemistry to determine whether melanocyte microphthalmia (Mi) is expressed which comprises:
   (a) contacting in vitro a biological specimen containing malignant cells with a monoclonal antibody that selectively binds to an epitope in the N-terminus Taq-Sac fragment of human melanocyte Mi; and
   (c) determining whether melanocyte Mi is being expressed in the specimen by the binding of the antibody to melanocyte Mi, wherein the expression of melanocyte Mi in a malignant cell is indicative of melanoma.

2. A method for screening for melanoma using immunohistochemistry to determine whether melanocyte microphthalmia (Mi) is expressed which comprises:
   (a) contacting in vitro a biological specimen containing malignant cells with an antibody raised against peptides comprising regions of human melanocyte microphthalmia (Mi) that selectively binds human melanocyte Mi: and
   (b) determining whether melanocyte Mi is being expressed in the specimen by the binding of the antibody to melanocyte Mi. wherein the expression of melanocyte Mi in a malignant cell is indicative of melanoma, wherein the antibody is a monoclonal antibody and wherein the antibody is generated using an epitope in the N-terminus Taq-Sac fragment of human melanocyte Mi.

3. The method of claim 1 or 2, wherein the biological specimen consists of malignant cells.

4. The method of claim 1 or 2, wherein the biological sample is on a slide.

5. The method of claim 1 or 2, wherein the antibody is used to determine where in the malignant cell said Mi is expressed.

* * * * *

UNITED STATES PATENT AND TRADEMARK OFFICE
CERTIFICATE OF CORRECTION

PATENT NO. : 7,338,767 B1 Page 1 of 1
APPLICATION NO. : 09/229283
DATED : March 4, 2008
INVENTOR(S) : David E. Fisher It is certified that error appears in the above-identified patent and that said Letters Patent is hereby corrected as shown below:

Column 23
At line 41, please replace "(c)" with -- (b) --

Column 24
At line 37, please replace "Mi." with -- Mi --

Signed and Sealed this

Tenth Day of February, 2009

JOHN DOLL
*Acting Director of the United States Patent and Trademark Office*

```
                         SEQUENCE LISTING

<160> NUMBER OF SEQ ID NOS: 10

<210> SEQ ID NO 1
<211> LENGTH: 21
<212> TYPE: DNA
<213> ORGANISM: MOUSE

<400> SEQUENCE: 1
ccgtctctgg aaacttgatc g                                              21

<210> SEQ ID NO 2
<211> LENGTH: 22
<212> TYPE: DNA
<213> ORGANISM: MOUSE

<400> SEQUENCE: 2
cgtgtatttt ccccacagag tc                                             22

<210> SEQ ID NO 3
<211> LENGTH: 20
<212> TYPE: DNA
<213> ORGANISM: MOUSE

<400> SEQUENCE: 3
gacatgcggt ggaacaaggg                                                20

<210> SEQ ID NO 4
<211> LENGTH: 20
<212> TYPE: DNA
<213> ORGANISM: MOUSE

<400> SEQUENCE: 4
gagctggaga tgcaggctag                                                20

<210> SEQ ID NO 5
<211> LENGTH: 20
<212> TYPE: DNA
<213> ORGANISM: MOUSE

<400> SEQUENCE: 5
gttgggaagg ttggctggac                                                20

<210> SEQ ID NO 6
<211> LENGTH: 21
<212> TYPE: DNA
<213> ORGANISM: MOUSE

<400> SEQUENCE: 6
ctgcctctct ttagccaatg c                                              21

<210> SEQ ID NO 7
<211> LENGTH: 23
<212> TYPE: DNA
<213> ORGANISM: MOUSE
```

```
<400> SEQUENCE: 7
ggatcatttg acttggggat cag                                               23

<210> SEQ ID NO 8
<211> LENGTH: 21
<212> TYPE: DNA
<213> ORGANISM: MOUSE

<400> SEQUENCE: 8
ctgtactctg agcagcaggt g                                                 21

<210> SEQ ID NO 9
<211> LENGTH: 22
<212> TYPE: DNA
<213> ORGANISM: MOUSE

<400> SEQUENCE: 9
gctctccggc atggtgccga gg                                                22

<210> SEQ ID NO 10
<211> LENGTH: 21
<212> TYPE: DNA
<213> ORGANISM: MOUSE

<400> SEQUENCE: 10
ctgtactctg agcagcaggt g                                                 21
```